US006531647B1

(12) United States Patent
Baulcombe et al.

(10) Patent No.: US 6,531,647 B1
(45) Date of Patent: **\*Mar. 11, 2003**

(54) GENE SILENCING METHODS

(75) Inventors: David Charles Baulcombe, Norwich (GB); Olivier Voinnet, Norwich (GB); Carsten Werner Lederer, Norwich (GB)

(73) Assignee: Plant Bioscience Limited, Norfolk (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/509,138

(22) PCT Filed: Sep. 22, 1998

(86) PCT No.: PCT/GB98/02862

§ 371 (c)(1), (2), (4) Date: Mar. 22, 2000

(87) PCT Pub. No.: WO99/15682

PCT Pub. Date: Apr. 1, 1999

(30) Foreign Application Priority Data

Sep. 22, 1997 (GB) .............................................. 9720148

(51) Int. Cl.[7] .............................................. C12N 15/82
(52) U.S. Cl. .................... 800/278; 536/23.72; 536/24.5
(58) Field of Search ............................. 536/24.5, 23.72, 536/23.2; 800/278; 435/468, 419, 6, 375

(56) References Cited

U.S. PATENT DOCUMENTS 6,077,992 A * 6/2000 Yadav

FOREIGN PATENT DOCUMENTS

| EP | 0 194 809 B1 | 9/1986 |
|---|---|---|
| EP | 0 425004 A2 | 5/1991 |
| WO | WO 91/13994 | 9/1991 |
| WO | WO 95/25801 | 9/1995 |
| WO | WO 95/34668 | * 12/1995 |
| WO | WO 97/02352 | 1/1997 |

OTHER PUBLICATIONS

Palauqui et al (1997) EMBO Journal 16:4738–4745.*
Angell et al (1997) EMBO Journal 16:3675–3684.*
Voinnet, et al., Systemic signalling in gene silencing, Nature, vol. 389, Oct. 9, 1997, XP–002097434.
Voinnet, et al., XP–002097435, Systemic Spread of Sequence–Specific Transgene RNA . . . , Cell, vol. 95, Oct. 16, 1998 pp. 177–187.
Angell, et al., The EMBO Journal, vol. 16 No. 12, pp. 3675–3684, 1997, Consistent gene silencing in transgenic plants expressing a replicating potato virus X RNA, XP–002067897.
Baulcombe, et al., Current Opinion in Biotechnology, 1996, pp. 173–180, XP–002067898, vol. 7.
Jorgensen, Science vol. 268, May 5, 1995, pp. 686–691.

* cited by examiner

Primary Examiner—Remy Yucel
Assistant Examiner—Bronwen M. Loeb
(74) Attorney, Agent, or Firm—Dann, Dorfman, Herrell & Skillman, P.C.

(57) ABSTRACT

Disclosed are methods for silencing a target nucleotide sequence (preferably representing one or more endogenous genes, preferably in a systemic fashion) which is present in a first part of the plant, which method comprises transiently introducing into the cytoplasm of a cell in a second part of the plant, which cell comprises a nucleic acid encoding the target sequence and which is remote from said first part of the plant, a nucleic acid construct.

25 Claims, 16 Drawing Sheets

Figure 1C:
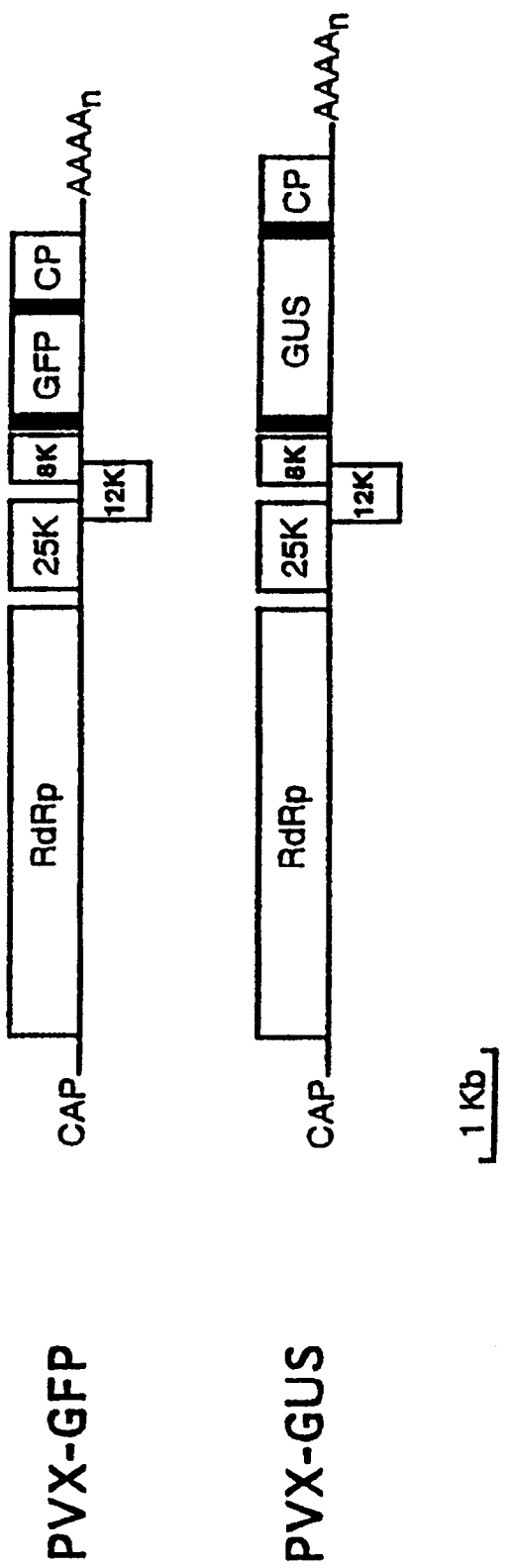

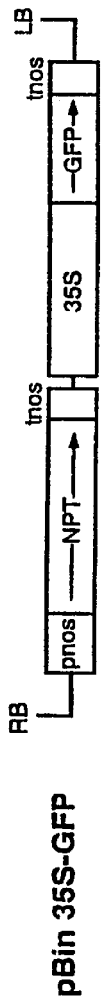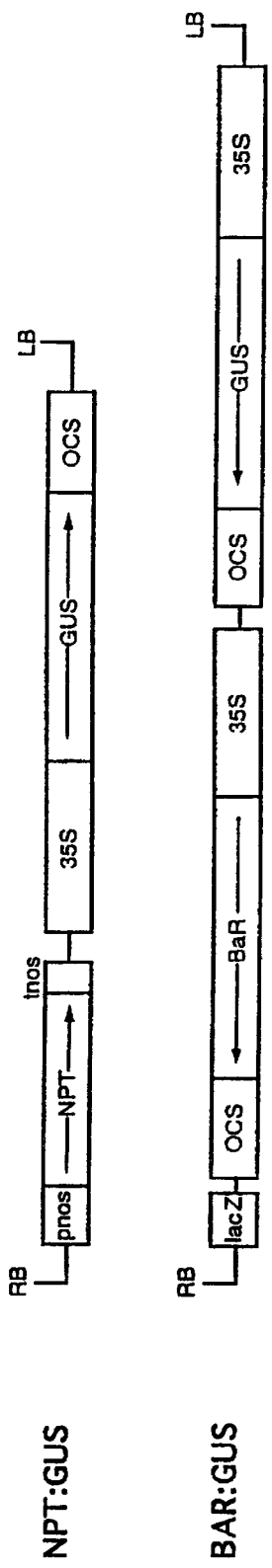
Fig. 1A
Fig. 1B

| Bombarded DNA | | % silenced plants | No. plants |
|---|---|---|---|
| pUC35S-GFP | [BamHI ClaI SalI; 35S \| G F P \| tnos] | 75 +/- 11 | 70 |
| GFP | [BamHI ClaI SalI; G F P] | 45 +/- 12 | 50 |
| ..P | [P] | 11 +/- 6 | 50 |
| G.. | [G] | 32 +/- 6 | 50 |

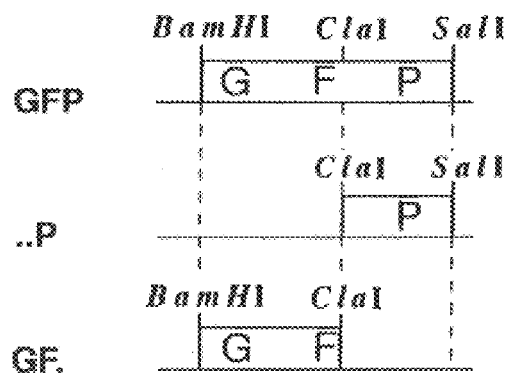
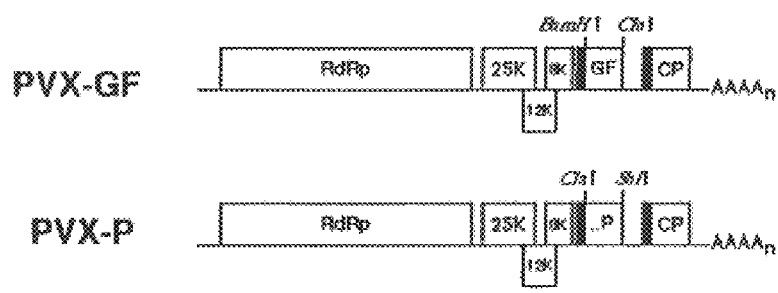
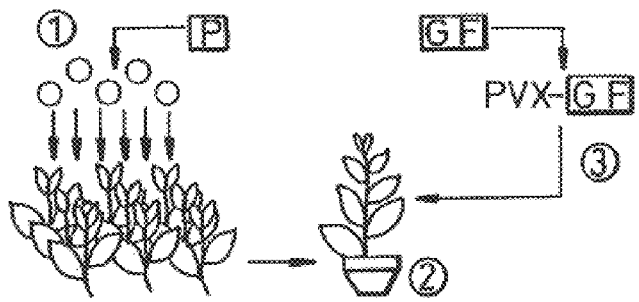
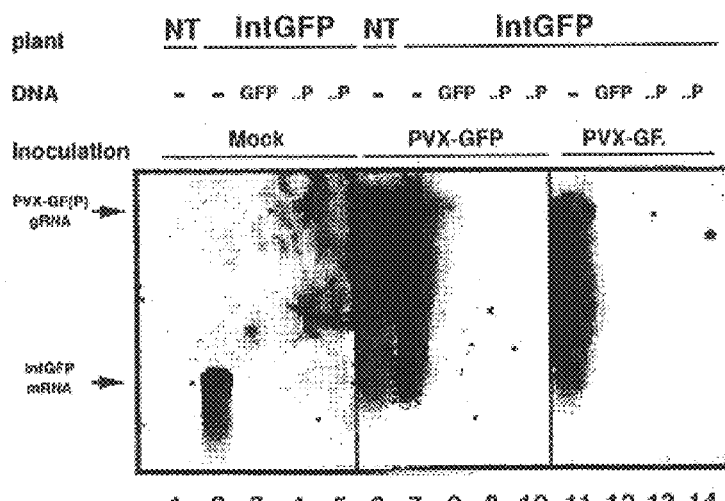
Fig. 7A
Fig. 7B progenitor construct: pPVX209 (in pUC19 vector)

pPVX210A

| 35S | -CaMV 35S promoter |
| Rep | -PVX replicase ORF |
| dRep | -5'-truncated PVX replicase ORF |
| 25 | -25-kDa ORF |
| d25 | -5'-truncated 25-kDa ORF |
| 12 | -12-kDa ORF |
| 8 | -8-kDa ORF |
| GFP | -GFP5 ORF |
| dGFP | -5'-truncated GFP ORF |
| CP | -coat protein ORF |
| CP sg pro | -duplicated subgenomic CP RNA promoter |
| dCP | -5'-truncated GFP ORF |
| NOS | -NOS terminator |

~/pUC19/35Spro/replicase-GCACAGATTTT<u>CCTAGG</u>     CACGTTATCAATTA
TGCGCCTGACTGGTGAAGGTCCCACTTTTGATGCAAACACTGAGTGCAACATAGCTTACAC
CCATACAAAGTTTGACATCCCAGCCGGAACTGCTCAAGTTTATGCAGGAGACGACTCCGCA
CTGGACTGTGTTCCAGAAGTGAAGCATAGTTTCCACAGGCTTGAGGACAAATTACTCCTAA
AGTCAAAGCCTGTAATCACGCAGCAAAAGAAGGGCAGTTGGCCTGAGTTTTGTGGTTGGCT
GATCACACCAAAAGGGGTGATGAAAGACCCAATTAAGCTCCATGTTAGCTTAAAATTGGCT
GAAGCTAAGGGTGAACTCAAGAAATGTCAAGATTCCTATGAAATTGATCTGAGTTATGCCT
ATGACCACAAGGACTCTCTGCATGACTTGTTCGATGAGAAACAGTGTCAGGCACACACACT
CACTTGCAGAACACTAATCAAGTCAGGGAGAGGCACTGTCTCACTTTCCCGCCTCAGAAAC
TTTCTTTAACCGTTAAGTTACCTTAGAGATTTGAATAAGATGGATATTCTCATCAGTAGTT
TGAAAAGTTTAGGTTATTCTAGGACTTCCAAATCTTTAGATTCAGGACCTTTGGTAGTACA
TGCAGTAGCCGGAGCCGGTAAGTCCACAGCCCTAAGGAAGTTGATCCTCAGACACCCAACA
TTCACCGTGCA-TGBsequence-AAACCATAA<u>GGGCCATTGCCGATCTCAAGCCACTCTC
CGTTGAACGGTTAAGTTTCCATTGATACTCGAAAGAGGTCAGCACCAGCTAGCATCGGAC</u>A
TGAAGACTAATCTTTTTCTCTTTCTCATCTTTTCACTTCTCCTATCATTATCCT<u>CGGCCG</u>
    AATT-GFP5sequence-ACATGACGAACTCTAAAT<u>GTCGAC</u>     CGCCGATAAGCT
TGATAGGGCCATTGCCGATCTCAAGCCACTCTCCGTTGAACGGTTAAGTTTCCATTGATAC
TCGAAAGATGTCAGCACCAGCTAGCACAACACAGCCCATAGGGTCAACTACCTCAACTACC
ACAAAAACTGCAGGCGCAACTCCTGCCACAGCTTCAGGCCTGTTCACCATCCCGGATGGGG
ATTTCTTTAGTACAGCCCGTGCCATAGTAGCCAGCAATGCTGTCGCAACAAATGAGGACCT
CAGCAAGATTGAGGCTATTTGGAAGGACATGAAGGTGCCCACAGACACTATGGCACAGGCT
GCTTGGGACTTAGTCAGACACTGTGCTGATGTAGGATCATCCGCTCAAACAGAAATGATAG
ATACAGGTCCCTATTCCAACGGCATCAGCAGAGCTAGACTGGCAGCAGCAATTAAAGAGGT
GTGCACACTTAGGCAATTTTGCATGAAGTATGCTCCAGTGGTATGGAACTGGATGTTAACT
AACAACAGTCCACCTGCTAACTGGCAAGCACAAGGTTTCAAGCCTGAGCACAAATTCGCTG
CATTCGACTTCTTCAATGGAGTCACCAACCCAGCTGCCATCATGCCCAAAGAGGGCTCAT
CCGGCCACCGTCTGAAGCTGAAATGAATGCTGCCCAAACTGCTGCCTTTGTGAAGATTACA
AAGGCCAGGGCACAATCCAACGACTTTGCCAGCCTAGATGCAGCTGTCA<u>CTCGAG</u>     GT
CGTATCACTGGAACAACAACCGCTGAGGCTGTTGTCACTCTACCACCACCATAA-/poly(
A)/NOSter/-

*Fig. 11A*

```
-/pUC19/35Spro/replicase-GCACAGATTTTCCTAGG     CACGTTATCAATTA
TGCGCCTGACTGGTGAAGGTCCCACTTTTGATGCAAACACTGAGTGCAACATAGCTTACAC
CCATACAAAGTTTGACATCCCAGCCGGAACTGCTCAAGTTTATGCAGGAGACGACTCCGCA
CTGGACTGTGTTCCAGAAGTGAAGCATAGTTTCCACAGGCTTGAGGACAAATTACTCCTAA
AGTCAAAGCCTGTAATCACGCAGCAAAAGAAGGGCAGTTGGCCTGAGTTTTGTGGTTGGCT
GATCACACCAAAAGGGGTGATGAAAGACCCAATTAAGCTCCATGTTAGCTTAAAATTGGCT
GAAGCTAAGGGTGAACTCAAGAAATGTCAAGATTCCTATGAAATTGATCTGAGTTATGCCT
ATGACCACAAGGACTCTCTGCATGACTTGTTCGATGAGAAACAGTGTCAGGCACACACACT
CACTTGCAGAACACTAATCAAGTCAGGGAGAGGCACTGTCTCACTTTCCCGCCTCAGAAAC
TTTCTTTAACCGTTAAGTTACCTTAGAGATTTGAATAAGATGGATATTCTCATCAGTAGTT
TGAAAAGTTTAGGTTATTCTAGGACTTCCAAATCTTTAGATTCAGGACCTTTGGTAGTACA
TGCAGTAGCCGGAGCCGGTAAGTCCACAGCCCTAAGGAAGTTGATCCTCAGACACCCAACA
TTCACCGTGCA-TGBsequence-AAACCATAAGGGCCATTGCCGATCTCAAGCCACTCTC
CGTTGAACGGTTAAGTTTCCATTGATACTCGAAAGAGGTCAGCACCAGCTAGCATCGGACA
TGAAGACTAATCTTTTTCTCTTTCTCATCTTTTCACTTCTCCTATCATTATCCTCGGCCG
    AATT-GFP5sequence-ACATGACGAACTCTAAATGTC
```

```
                                                             GAG  GT
CGTATCACTGGAACAACAACCGCTGAtGCTGTTGTCACTCTACCACCACCATAA-/poly(
A)/NOSter/-
```

*Fig. 11B*

```
~/pUC19/35Spro/replicase~GCACAGATTTTCCTAGG        CACGTTATCAATTA
TGCGCCTGACTGGTGAAGGTCCCACTTTTGATGCAAACACTGAGTGCAACATAGCTTACAC
CCATACAAAGTTTGACATCCCAGCCGGAACTGCTCAAGTTTATGCAGGAGACGACTCCGCA
CTGGACTGTGTTCCAtAAGTGAAGCATAGTTTCCACAGGCTTGAGGACAAATTACTCCTAA
AGTCAAAGCCTGTAATCACGCAGCAAAAGAAGGGCAGTTGGCCTGAGTTTTGTGGTTGGCT
GATCACACCAAAAGGGGTGATGAAAGACCCAATTAAGCTCCATGTTAGCTTAAAATTGGCT
GAAGCTAAGGGTGAACTCAAGAAATGTCAAGATTCCTATGAAATTGATCTGAGTTATGCCT
ATGACCACAAGGACTCTCTGCATGACTTGTTCGATGAGAAACAGTGTCAGGCACACACACT
CACTTGCAtAACACTAATCAAGTCAGGGAGAGGCACTGTCTCACTTTCCCGCCTCAGAAAC
TTTCTTTAACCG CGGCCG
   AATT~GFP5sequence~ACATGACGAACTCTAAATGTCGAG    GTCGTATCACTG
GAACAACAACCGCTGATGCTGTTGTCACTCTACCACCACCATAA~/poly(A)/NOSter/
~
```

Fig. 11C

~/pUC19/35Spro/replicase~GCACAGATTTTCCTAGG    CACGTTATCAATTA
TGCGCCTGACTGGTGAAGGTCCCACTTTTGATGCAAACACTGAGTGCAACATAGCTTACAC
CCATACAAAGTTTGACATCCCAGCCGGAACTGCTCAAGTTTATGCAGGAGACGACTCCGCA
CTGGACTGTGTTCCAtAAGTGAAGCATAGTTTCCACAGGCTTGAGGACAAATTACTCCTAA
AGTCAAAGCCTGTAATCACGCAGCAAAAGAAGGGCAGTTGGCCTGAGTTTTGTGGTTGGCT
GATCACACCAAAAGGGGTGATGAAAGACCCAATTAAGCTCCATGTTAGCTTAAAATTGGCT
GAAGCTAAGGGTGAACTCAAGAAATGTCAAGATTCCTATGAAATTGATCTGAGTTATGCCT
ATGACCACAAGGACTCTCTGCATGACTTGTTCGATGAGAAACAGTGTCAGGCACACACACT
CACTTGCAGAACACTAATCAAGTCAGGGAGAGGCACTGTCTCACTTTCCCGCCTCAGAAAC
TTTCTTTAACCGTTAAGTTACCTTAGAGATTTGAATAAGATGGATATTCTCATCAGTAGTT
TGAAAAGTTTAGGTTATTCTAGGACTTCCAAATCTTTAGATTCAGGACCTTTGGTAGTACA
TGCAGTAGCCGGAGCCGGTAAGTCCACAGCCCTAAGGAAGTTGATCCTCAGACAC CGGCCG
    AATT~GFP5sequence~ACATGACGAACTCTAAATGTCGAG    GTCGTATCACTG
GAACAACAACCGCTGATGCTGTTGTCACTCTACCACCACCATAA~/poly(A)/NOSter/
~

Fig. 11D

~/pUC19/35Spro/replicase~GCACAGATTTTCCTAGG    CACGTTATCAATTA
TGCGCCTGACTGGTGAAGGTCCCACTTTTGATGCAAACACTGAGTGCAACATAGCTTACAC
CCATACAAAGTTTGACATCCCAGCCGGAACTGCTCAAGTTTATGCAGGAGACGACTCCGCA
CTGGACTGTGTTCCAtAAGTGAAGCATAGTTTCCACAGGCTTGAGGACAAATTACTCCTAA
AGTCAAAGCCTGTAATCACGCAGCAAAAGAAGGGCAGTTGGCCTGAGTTTTGTGGTTGGCT
GATCACACCAAAAGGGGTGATGAAAGACCCAATTAAGCTCCATGTTAGCTTAAAATTGGCT
GAAGCTAAGGGTGAACTCAAGAAATGTCAAGATTCCTATGAAATTGATCTGAGTTATGCCT
ATGACCACAAGGACTCTCTGCATGACTTGTTCGATGAGAAACAGTGTCAGGCACACACACT
CACTTGCAGAACACTAATCAAGTCAGGGAGAGGCACTGTCTCACTTTCCCGCCTCAGAAAC
TTTCTTTAACCGTTAAGTTACCTTAGAGATTTGAATAAG CGGCCG
    AATT~GFP5sequence~ACATGACGAACTCTAAATGTCGAG    GTCGTATCACTG
GAACAACAACCGCTGATGCTGTTGTCACTCTACCACCACCATAA~/poly(A)/NOSter/
~

Fig. 11E

```
~/pUC19/35Spro/replicase-GCACAGATTTTCCTAGG      CACGTTATCAATTA
TGCGCCTGACTGGTGAAGGTCCCACTTTTGATGCAAACACTGAGTGCAACATAGCTTACAC
CCATACAAAGTTTGACATCCCAGCCGGAACTGCTCAAGTTTATGCAGGAGACGACTCCGCA
CTGGACTGTGTTCCAGAAGTGAAGCATAGTTTCCACAGGCTTGAGGACAAATTACTCCTAA
AGTCAAAGCCTGTAATCACGCAGCAAAAGAAGGGCAGTTGGCCTGAGTTTTGTGGTTGGCT
GATCACACCAAAAGGGGTGATGAAAGACCCAATTAAGCTCCATGTTAGCTTAAAATTGGCT
GAAGCTAAGGGTGAACTCAAGAAATGTCAAGATTCCTATGAAATTGATCTGAGTTATGCCT
ATGACCACAAGGACTCTCTGCATGACTTGTTCGATGAGAAACAGTGTCAGGCACACACACT
CACTTGCAGAACACTAATCAAGTCAGGGAGAGGCACTGTCTCACTTTCCCGCCTCAGAAAC
TTTCTTTAACCGctagcGGGCCATTGCCGATCTCAAGCCACTCTCCGTTGAACGGTTAAGT
TTCCATTGATACTCGAAAGAGGTCAGCACCAGCTAGCATCGGACATGAAGACTAATCTTTT
TCTCTTTCTCATCTTTTCACTTCTCCTATCATTATCCT_____
_____
_____CGGCCG
   AATT-GFP5sequence-ACATGACGAACTCTAAATGTCGAG      GTCGTATCACTG
GAACAACAACCGCTGATGCTGTTGTCACTCTACCACCACCATAA~/poly(A)/NOSter/
~
```

*Fig. 11F*

SEQUENCE LISTING

```
<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 1
ggatccaagg agatataaca a                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 2
aaatcgattc ccttaagctc g                                              21

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 3
agcttaaggg aatcgat                                                   17

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 4
cttagagttc gtcatgtttg t                                              21

<210> SEQ ID NO 5
<211> LENGTH: 18
<212> TYPE: DNA
<213> ORGANISM: Artificial Sequence
<220> FEATURE:
```

<223> OTHER INFORMATION: Description of Artificial Sequence: Primer

<400> SEQUENCE: 5
ttgtggccga ggatgttt                                             18

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
aaatcgatcc cttaagctcg                                           20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
gggtaacgcc agggttttcc                                           20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
agtagtgaca agtgttggcc                                           20

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 9
agcgggcgct agggcgct                                             18

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 10
tgacagaaaa tttgtgccca tt                                        22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 11
gtaaagcact aaatcggaac c                                         21

```
<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 12
ttgggacaac tccagtgaaa a                                              21

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 13
ccactacgtg aaccatcac                                                 19

<210> SEQ ID NO 14
<211> LENGTH: 713
<212> TYPE: DNA
<213> ORGANISM: Artificial Sequence
<220> FEATURE:
<223> OTHER INFORMATION: Description of Artificial Sequence: Synthetic
      sequence

<400> SEQUENCE: 14
gcacagattt tcctaggcac gttatcaatt atgcgcctga ctggtgaagg tcccactttt    60
gatgcaaaca ctgagtgcaa catagcttac acccatacaa gtttgacat cccagccgga   120 actgctcaag tttatgcagg agacgactcc gcactggact gtgttccaga agtgaagcat   180
agtttccaca ggcttgagga caaattactc ctaaagtcaa agcctgtaat cacgcagcaa   240
aagaagggca gttggcctga gttttgtggt tggctgatca caccaaaagg ggtgatgaaa   300
gacccaatta agctccatgt tagcttaaaa ttggctgaag ctaagggtga actcaagaaa   360
tgtcaagatt cctatgaaat tgatctgagt tatgcctatg accacaagga ctctctgcat   420
gacttgttcg atgagaaaca gtgtcaggca cacacactca cttgcagaac actaatcaag   480
tcagggagag gcactgtctc actttcccgc ctcagaaact ttctttaacc gttaagttac   540
cttagagatt tgaataagat ggatattctc atcagtagtt tgaaaagttt aggttattct   600
aggacttcca aatctttaga ttcaggacct ttggtagtac atgcagtagc cggagccggt   660
aagtccacag ccctaaggaa gttgatcctc agacacccaa cattcaccgt gca           713

<210> SEQ ID NO 15
<211> LENGTH: 162
<212> TYPE: DNA
<213> ORGANISM: Artificial Sequence
<220> FEATURE:
<223> OTHER INFORMATION: Description of Artificial Sequence: Synthetic
      sequence

<400> SEQUENCE: 15
aaaccataag ggccattgcc gatctcaagc cactctccgt tgaacggtta agtttccatt    60
gatactcgaa agaggtcagc accagctagc atcggacatg aagactaatc tttttctctt   120
tctcatcttt tcacttctcc tatcattatc ctcggccgaa tt                      162

<210> SEQ ID NO 16
<211> LENGTH: 818
<212> TYPE: DNA
```

```
<213> ORGANISM: Artificial Sequence
<220> FEATURE:
<223> OTHER INFORMATION: Description of Artificial Sequence: Synthetic
      sequence

<400> SEQUENCE: 16
acatgacgaa ctctaaatgt cgaccgccga taagcttgat agggccattg ccgatctcaa     60
gccactctcc gttgaacggt taagtttcca ttgatactcg aaagatgtca gcaccagcta    120
gcacaacaca gcccataggg tcaactacct caactaccac aaaaactgca ggcgcaactc    180
ctgccacagc ttcaggcctg ttcaccatcc cggatgggga tttctttagt acagcccgtg    240
ccatagtagc cagcaatgct gtcgcaacaa atgaggacct cagcaagatt gaggctattt    300
ggaaggacat gaaggtgccc acagacacta tggcacaggc tgcttgggac ttagtcagac    360
actgtgctga tgtaggatca tccgctcaaa cagaaatgat agatacaggt ccctattcca    420
acggcatcag cagagctaga ctggcagcag caattaaaga ggtgtgcaca cttaggcaat    480
tttgcatgaa gtatgctcca gtggtatgga actggatgtt aactaacaac agtccacctg    540
ctaactggca agcacaaggt ttcaagcctg agcacaaatt cgctgcattc gacttcttca    600
atggagtcac caacccagct gccatcatgc ccaaagaggg gctcatccgg ccaccgtctg    660
aagctgaaat gaatgctgcc caaactgctg cctttgtgaa gattacaaag gccagggcac    720
aatccaacga ctttgccagc ctagatgcag ctgtcactcg aggtcgtatc actggaacaa    780
caaccgctga ggctgttgtc actctaccac caccataa                            818

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      sequence

<400> SEQUENCE: 17
acatgacgaa ctctaaatgt c                                                21

<210> SEQ ID NO 18
<211> LENGTH: 56
<212> TYPE: DNA
<213> ORGANISM: Artificial Sequence
<220> FEATURE:
<223> OTHER INFORMATION: Description of Artificial Sequence: Synthetic
      sequence

<400> SEQUENCE: 18
gtcgtatcac tggaacaaca accgctgatg ctgttgtcac tctaccacca ccataa          56

<210> SEQ ID NO 19
<211> LENGTH: 531
<212> TYPE: DNA
<213> ORGANISM: Artificial Sequence
<220> FEATURE:
<223> OTHER INFORMATION: Description of Artificial Sequence: Synthetic
      sequence

<400> SEQUENCE: 19
gcacagattt tcctaggcac gttatcaatt atgcgcctga ctggtgaagg tcccactttt     60
gatgcaaaca ctgagtgcaa catagcttac acccatacaa agtttgacat cccagccgga    120
actgctcaag tttatgcagg agacgactcc gcactggact gtgttccata agtgaagcat    180
agtttccaca ggcttgagga caaattactc ctaaagtcaa agcctgtaat cacgcagcaa    240
```

-continued

```
aagaagggca gttggcctga gttttgtggt tggctgatca caccaaaagg ggtgatgaaa    300
gacccaatta agctccatgt tagcttaaaa ttggctgaag ctaagggtga actcaagaaa    360
tgtcaagatt cctatgaaat tgatctgagt tatgcctatg accacaagga ctctctgcat    420
gacttgttcg atgagaaaca gtgtcaggca cacacactca cttgcataac actaatcaag    480
tcagggagag gcactgtctc actttcccgc ctcagaaact ttctttaacc g             531
```

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic sequence

<400> SEQUENCE: 20

```
cggccgaatt                                                            10
```

<210> SEQ ID NO 21
<211> LENGTH: 80
<212> TYPE: DNA
<213> ORGANISM: Artificial Sequence
<220> FEATURE:
<223> OTHER INFORMATION: Description of Artificial Sequence: Synthetic sequence

<400> SEQUENCE: 21

```
acatgacgaa ctctaaatgt cgaggtcgta tcactggaac aacaaccgct gatgctgttg    60
tcactctacc accaccataa                                                 80
```

<210> SEQ ID NO 22
<211> LENGTH: 696
<212> TYPE: DNA
<213> ORGANISM: Artificial Sequence
<220> FEATURE:
<223> OTHER INFORMATION: Description of Artificial Sequence: Synthetic sequence

<400> SEQUENCE: 22

```
gcacagattt tcctaggcac gttatcaatt atgcgcctga ctggtgaagg tcccactttt    60
gatgcaaaca ctgagtgcaa catagcttac acccatacaa agtttgacat cccagccgga    120
actgctcaag tttatgcagg agacgactcc gcactggact gtgttccata agtgaagcat    180
agtttccaca ggcttgagga caaattactc ctaaagtcaa agcctgtaat cacgcagcaa    240
aagaagggca gttggcctga gttttgtggt tggctgatca caccaaaagg ggtgatgaaa    300
gacccaatta agctccatgt tagcttaaaa ttggctgaag ctaagggtga actcaagaaa    360
tgtcaagatt cctatgaaat tgatctgagt tatgcctatg accacaagga ctctctgcat    420
gacttgttcg atgagaaaca gtgtcaggca cacacactca cttgcagaac actaatcaag    480
tcagggagag gcactgtctc actttcccgc ctcagaaact ttctttaacc gttaagttac    540
cttagagatt tgaataagat ggatattctc atcagtagtt tgaaaagttt aggttattct    600
aggacttcca aatctttaga ttcaggacct tggtagtac atgcagtagc cggagccggt    660
aagtccacag ccctaaggaa gttgatcctc agacac                              696
```

<210> SEQ ID NO 23
<211> LENGTH: 558
<212> TYPE: DNA
<213> ORGANISM: Artificial Sequence
<220> FEATURE:
<223> OTHER INFORMATION: Description of Artificial Sequence: Synthetic sequence

<400> SEQUENCE: 23

```
gcacagattt tcctaggcac gttatcaatt atgcgcctga ctggtgaagg tcccactttt      60
gatgcaaaca ctgagtgcaa catagcttac acccatacaa agtttgacat cccagccgga     120
actgctcaag tttatgcagg agacgactcc gcactggact gtgttccata agtgaagcat     180
agtttccaca ggcttgagga caaattactc ctaaagtcaa agcctgtaat cacgcagcaa     240
aagaagggca gttggcctga gttttgtggt tggctgatca caccaaaagg ggtgatgaaa     300
gacccaatta agctccatgt tagcttaaaa ttggctgaag ctaagggtga actcaagaaa     360
tgtcaagatt cctatgaaat tgatctgagt tatgcctatg accacaagga ctctctgcat     420
gacttgttcg atgagaaaca gtgtcaggca cacacactca cttgcagaac actaatcaag     480
tcagggagag gcactgtctc actttcccgc ctcagaaact ttctttaacc gttaagttac     540
cttagagatt tgaataag                                                   558
```

<210> SEQ ID NO 24
<211> LENGTH: 679
<212> TYPE: DNA
<213> ORGANISM: Artificial Sequence
<220> FEATURE:
<223> OTHER INFORMATION: Description of Artificial Sequence: Synthetic sequence

<400> SEQUENCE: 24

```
gcacagattt tcctaggcac gttatcaatt atgcgcctga ctggtgaagg tcccactttt      60
gatgcaaaca ctgagtgcaa catagcttac acccatacaa agtttgacat cccagccgga     120
actgctcaag tttatgcagg agacgactcc gcactggact gtgttccaga agtgaagcat     180
agtttccaca ggcttgagga caaattactc ctaaagtcaa agcctgtaat cacgcagcaa     240
aagaagggca gttggcctga gttttgtggt tggctgatca caccaaaagg ggtgatgaaa     300
gacccaatta agctccatgt tagcttaaaa ttggctgaag ctaagggtga actcaagaaa     360
tgtcaagatt cctatgaaat tgatctgagt tatgcctatg accacaagga ctctctgcat     420
gacttgttcg atgagaaaca gtgtcaggca cacacactca cttgcagaac actaatcaag     480
tcagggagag gcactgtctc actttcccgc ctcagaaact ttctttaacc gctagcgggc     540
cattgccgat ctcaagccac tctccgttga acggttaagt ttccattgat actcgaaaga     600
ggtcagcacc agctagcatc ggacatgaag actaatcttt ttctctttct catcttttca     660
cttctcctat cattatcct                                                  679
```

GENE SILENCING METHODS

TECHNICAL FIELD

The present invention relates to methods and materials for controlling gene silencing in plants, and various processes and products employing these methods and materials.

PRIOR ART

Co-suppression and Anti-sense Suppression of Endogenous Genes

It is known that stably-integrated transgenes (referred to as 'STgenes' or 'intGENES' below) which may be constitutively expressed may be used to suppress homologous endogenous ('HEgenes') plant genes. This was discovered originally when chalcone synthase transgenes in petunia caused suppression of the endogenous chalcone synthase genes. Subsequently it has been described how many, if not all plant genes can be "silenced" by transgenes. Gene silencing requires sequence homology between the transgene and the gene that becomes silenced (Matzke, M. A. and Matzke, A. J. M. (1995), *Trends in Genetics,* 11: 1–3). This sequence homology may involve promoter regions or coding regions of the silenced gene (Matzke, M. A. and Matzke, A. J. M. (1993) *Annu. Rev. Plant Physiol. Plant Mol. Biol.,* 44: 53–76, Vaucheret, H. (1993) *C. R. Acad. Sci. Paris,* 316: 1471–1483, Vaucheret, H. (1994), *C. R. Acad. Sci. Paris,* 317: 310–323, Baulcombe, D. C. and English, J. J. (1996), Current Opinion In Biotechnology, 7: 173–180, Park, Y-D., et al (1996), *Plant J.,* 9: 183–194).

When coding regions are involved, the transgene able to cause gene silencing may have been constructed with a promoter that would transcribe either the sense or the antisense orientation of the coding sequence RNA. In at least one example the coding sequence transgene was constructed without a promoter (Van Blokland, R., et al (1994), *Plant J.,* 6: 861–877).

Co-suppression of Transgenes

It has also become clear that gene silencing (gs) can account for some characteristics of transgenic plants that are not easily reconciled with conventional understanding of genetics. For example the wide variation in STgene expression between sibling lines with a Stgene construct is due in part to gene silencing: low expressers are those with a high level of gene silencing whereas high expressers are those in which gene silencing is absent or induced late in plant development. In this case there is no requirement for there to be an HEgene corresponding to the STgene (see e.g., Elamayan & Vaucheret (1996) Plant J., 9: 787–797.

Viral Resistance

In addition to observations of STgenes, gs has also been implicated in virus resistance. In these cases various factors including ectopic DNA interactions[6], DNA methylation[7], transgene expression level[8] and double stranded RNA[9] have been proposed as initiators of gene silencing.

Additionally in non-transgenic plants, it has been demonstrated that leaves which develop subsequently to systematic spread of a virus in a plant contain lower levels of virus than do symptomatic leaves. This resistance may be similar in nature to transgene-induced gene silencing (see e.g. Ratcliff et al (1997) *Science,* 276: 1558–1560).

Cytoplasmically Replicating Viral Constructs

Biosource Technologies, in WO 95/34668, have suggested the use of genetic constructions based on RNA viruses which replicate in the cytoplasm of cells to provide inhibitory RNA, either anti-sense or sense ("co-suppressor") RNA. The constructs were used to inhibit a particular HEgene (phytoene desaturase). Cells were transfected with the cytoplasmically-replicating genetic constructions in which the RNA encoding region is specific for the gene of interest. The hybrid viruses spread throughout the plant, including the non-inoculated upper leaves (as verified by transmission electron microscopy). System-wide gene silencing was reported following transfection.

GB patent application 9703146.2, and PCT/GB98/00442, both filed in the name of John Innes Centre Innovations Limited, are hereby incorporated by reference. These applications, which were not published prior to the claimed priority date of the present application, discuss various constructs ('amplicons') which are intended to be stably integrated into the plant genome, and to generate cytoplasmically replicating constructs which are capable of eliciting gene silencing.

Silencing in Animals

Fire et al (1998) Nature 391: 806–811 (not published prior to the claimed priority date of the present application) discusses the use of RNA, particularly double-stranded RNA, to achieve silencing of endogenous genes and GFP-transgenes in nematodes. The demonstrated interference effect was apparently able to cross cell-boundaries.

Applications for Gene-silencing

In principle there is an enormous practical potential of gs for crop improvement. It is possible to silence genes conferring unwanted traits in the plant by transformation with transgene constructs containing elements of these genes. Examples of this type of application include gs of ripening specific genes in tomato to improve processing and handling characteristics of the harvested fruit; gs of genes involved in pollen formation so that breeders can reproducibly generate male sterile plants for the production of F1 hybrids; gs of genes involved in lignin biosynthesis to improve the quality of paper pulp made from vegetative tissue of the plant; gene silencing of genes involved in flower pigment production to produce novel flower colours; gene silencing of genes involved in regulatory pathways controlling development or environmental responses to produce plants with novel growth habit or (for example) disease resistance; elimination of toxic secondary metabolites by gene silencing of genes required for toxin production.

Gene silencing is also useful for investigating gene function in that it can be used to impose an intermediate or a null phenotype for a particular gene, which can provide information about the function of that gene in vivo.

A major complication in the practical exploitation of this phenomenon to date is the unpredictable and low occurrence of gene silencing. Therefore, it has not been realistic to attempt gene silencing in plants that are difficult to transform and for which it is difficult to produce many transformants. Similarly, it would be difficult to activate (and deactivate) gene silencing against several different traits or against several viruses in the same plant. Even with plants that are easy to transform the need to generate multiple lines limits the ease of exploitation of gene silencing.

INVENTION

The present inventors have now demonstrated a novel means of providing consistent, controlled, systemic gene silencing within a system, particularly a mature plant, which may (but is preferably not) a transgenic plant. This novel approach is clearly distinct from previously described approaches to gene silencing, for example, transwitch and antisense technologies, in that it describes a multicomponent system in which there is the potential to regulate the gene silencing spatially and optionally temporally.

The current invention is also distinct from the virus-induced gene silencing described previously by Biosource Technologies. In the current invention there is no absolute requirement that the transgenes conferring the gene silencing or their transcripts are able to replicate using viral components or through mechanisms that resemble virus replication, although in certain advantageous embodiments they may do so. Importantly, the systemic silencing of the invention does not require that the transgenes or their transcripts use virus-derived mechanisms to move between cells (e.g. 'movement proteins' as they are termed in the art).

These movement proteins are encoded by most (probably nearly all) plant viruses. Movement proteins are normally recognised by mutation analysis of a viral genome. Mutation of a movement protein gene affects the ability of a virus to spread in the infected plant but does not affect the ability of the virus to replicate. Examples of viral movement proteins identified in this way include the 30 kDa protein of tobacco mosaic virus (Deom et al., 1987), the 25 kDa, 12 kDa and 8 kDa triple gene block proteins of potato virus X (FIG. 1C) (Angell and Baulcombe, 1995; Angell et al., 1996; Verchot et al., 1998) and the tubule-forming protein of cowpea mosaic virus (van Lent et al., 1991). Some viruses also encode movement proteins specifically for translocation of the virus through the phloem of the plant. Examples of these long distance movement proteins include the 2b protein encoded in cucumber mosaic virus (Ding et al., 1995) and the 19 kDa protein of tomato bushy stunt virus (Scholthof et al., 1995).

Until recently it has been considered that movement proteins open channels between plant cells and thereby mediate virus movement (Wolf et al., 1989). However it is now apparent that at least some of these proteins may also promote movement by suppression of a defence mechanism in the plant that blocks virus movement, which may itself be related to the gene silencing referred to hereinbefore. From these new findings, which are consistent with observations by Anandalakshmi et al. (1998) and Brigneti et al. (1998) [both in press] it is clear that movement proteins may be suppressors of gene silencing. Similarly the work of the present inventors suggests that certain proteins previously described only as pathogenicity proteins may also have a role in suppressing a gene silencing signal.

Thus it can be appreciated that stronger, systemic, gene silencing is obtained if transgene constructs for gene silencing do not also lead to expression of gene silencing by viral movement proteins or pathogenicity proteins, which are a fundamental part of the prior art systems which rely on the activity of vectors based on RNA-viruses. Such systems may be incapable of mediating a TIGS effect (see e.g. Dougherty, W. G, et al Molecular Plant-Microbe Interactions, 1994: 7, 544–552).

The novel gene silencing system of this invention was first demonstrated using transgenic *N. benthamiana* stably transformed with stably transformed with the gene for green fluorescent protein (designated stGFP).

The workers demonstrated that the expression of stGFP could be silenced by the transient presence of a GFP reporter gene (which was designated trGFP to distinguish it from the stGFP) using strains of *Agrobacterium tumefaciens* carrying binary Ti plasmid vectors or using direct infiltration. The silencing was systemic in nature, occurring remotely from the sites of infection or infiltration.

This approach has suggested the existence of a previously unknown signalling mechanism in plants that mediates systemic gene silencing. The signal of silencing is gene-specific and likely to be a nucleic acid that moves between cells.

A systemic, sequence-specific signal of gene silencing which is initiated by the transient presence (not stable integration) in part of a plant of foreign initiator nucleic acid or nucleic acid complex (termed hereinafter 'fiNA') which need not be capable of autonomous replication in the cytoplasm of a plant cell or movement from cell to cell, but which generates a signal which may be propagated systemically is an entirely novel and unexpected concept in plant biology. The observation has a number of important (industrially applicable) properties. These properties, and the characteristics of the fiNA required achieve them, will be discussed in more detail hereinafter.

The work of the present inventors, with hindsight, is consistent with data from other published experimental systems and could be a general feature of gene silencing in plants.

Thus transgenic petunia exhibiting transgene-induced silencing of the genes required for flower pigment biosynthesis were shown to exhibit unusual and irregular patterns of pigmentation. These can perhaps be explained by an extracellular signal rather than by cell lineage-dependent cues of gene silencing (see Jorgensen (1995) *Science* 268, 686–691). It should be stressed that in that work the gene silencing of an HEgene (CHS) was induced in the test plants using a chimeric STgene. Although the paper speculates about a 2 state system of gene silencing, no information is given about how to switch gene silencing on.

Work by a different group demonstrated chitinase gene silencing in non-clonal sectors of transgenic tobacco (see Kunz et al (1996) *Plant J.* 10, 4337–450.). This work demonstrated both the 'self' inactivation of the expression of STgenes alone, plus inactivation of HEgenes by STgenes. The work also suggested that gene silencing was a post-transcriptional event. It was demonstrated that gene silencing occurred stochastically in progeny of transgenic plants but that 'resetting' to the non-silenced state occurred non-stochastically in developing seeds. These observations, plus the variegated pattern of silencing shown by some plants, demonstrated that the gene silencing phenotype was not merely a lineage event, but also highlighted the unpredictability of gene silencing. There is no suggestion in the paper of the use of fiNA to control gene silencing in non-silenced or 'reset' genes.

Palaqui et al, in The EMBO Journal (1997) V 16 No 15: pg 4738, demonstrated that grafting non-silenced scions onto gs-stock (co-suppressed ST and HE nitrate reductase genes,) imposes silencing on the scion. The scion had to contain the STgene, and the silencing was unidirectional and could occur through a wild-type stem 'barrier' in which HE nitrate reductase genes are present and function as signal transducing resident genes. Although a diffusible messenger is postulated, there is no mention of generating or employing this messenger other than by the use of grafts of already-silenced homozygous plant stock.

The systemic signal demonstrated by the present inventors is also consistent with recent findings that gene silencing is associated with induced natural defence against viruses. The signal could move in the plant ahead of the inducing virus so that anti-viral gene silencing could delay spread of the infection front (Ratcliff et al (1997) *Science*, 276: 1558–1560). The data below also suggests that in certain situations, viral proteins may act to inhibit this signal propagation.

The provision of the signalling mechanism and the novel means by which it can be activated (transient presence of fiNA) opens up a number of possibilities which will be discussed in more detail hereinafter; essentially the ability to conveniently control gene silencing systemically will be useful both in the investigation of gene function, and the production of gene silencing plants, as well as in the investigation of the mechanisms of gene silencing.

Particularly useful is the ability to rapidly and consistently impose, at will, gene silencing on HE or STgenes of known or unknown function in order to investigate their phenotype.

Although the systemic signal is not yet structurally characterised, a number of points about it can be made in the light of the present work. It is produced when fiNA is introduced in to a plant cell, particularly directly or indirectly into the cytoplasm, where the target gene or possibly a resident gene (as defined below) which is to be silenced is being transcribed, in the same plant cell, and there is sequence similarity between the coding regions of fiNA and target gene.

These findings suggest that a protein product, or the corresponding DNA or RNA, is a component of the signal. Of these, the protein product is the least plausible candidate because there is no mechanism known that explains how it could move systemically and specifically target the RNAs of the target. However, a nucleic acid-based signal could mediate sequence-specific gene silencing via a base-paired or triple helical structure with the target gene RNA (or the transcription product of homologous resident gene) as it moved between cells and tissues expressing that gene. Moreover, a nucleic acid could move in the plant, perhaps using the channels involved in virus or viroid movement. The demonstrated systemic spread of ST-GFP silencing (FIG. 2c) is consistent with this suggestion because it follows a course (FIGS. 2c, 2g) that is similar to the pattern of virus spread in an infected plant.

Thus in a first aspect of the invention there is disclosed a method for silencing a target nucleotide sequence (e.g. a gene) in a plant comprising transiently introducing (i.e. not via a stably integrated transgene) into the cytoplasm of cells of that plant in which the target sequence is present (and preferably being transcribed) a foreign initiator nucleic acid (fiNA) which is:

(i) incapable of movement from cell to cell, and
(ii) optionally incapable of autonomous replication, and
(iii) has sequence homology with the gene to be silenced.

This method is used for silencing a target gene in a first part of a plant comprising the steps of:

(a) transiently exposing a second part of the plant, remote from said first part, to a foreign initiator nucleic acid (fiNA) as described above such as to generate a gene silencing signal,
(b) causing or allowing the signal to be propagated to the second part of the plant such as to silence said target gene.

"Causing or allowing" in this sense implies, in particular, that the construct giving rise to the fiNA (and hence signal) does not encode proteins which would block the signal e.g. movement proteins such as those which permit viral movement from cell to cell.

Thus the present inventors have demonstrated for the first time Transiently Induced Gene Silencing (or 'TIGS'). They have further demonstrated that a signal capable of propagating gene silencing can be initiated in a second part of the plant to induce silencing of a gene in the first.

Generally speaking, TIGS can be considered as having three phases:

(i) initiation of a gene silencing signal by the transient presence of fiNA in the cytoplasm of plant cells, which is described in more detail below,
(ii) translocation of a gene silencing signal (though not the fiNA itself) through tissues of the plant, which is facilitated by the expression of a HE gene or a ST gene with homology to the target gene in those tissues,
(iii) maintenance of the gene silencing signal within the cells of the plant, which may be remote from those which were initially, transiently, exposed to the fiNA.

The various different features of TIGS will now be discussed in more detail:

"Silencing" in this context is used to refer to suppression of expression of the (target) gene. It does not necessarily imply reduction of transcription, because gene silencing is believed to operate in at least some cases post-transcriptionally. The degree of reduction may be so as to totally abolish production of the encoded gene product (yielding a null phenotype), but more generally the abolition of expression may be partial, with some degree of expression remaining (yielding an intermediate phenotype). The term should not therefore be taken to require complete "silencing" of expression. It is used herein where convenient because those skilled in the art well understand this.

The "systemic" silencing means that the target gene is silenced via a signal which is translocated substantially throughout the tissues of a plant (though certain tissues may not be silenced e.g. meristematic tissues, as discussed in more detail below).

The "target" gene (ie the gene to be silenced or the silenced gene) in the present invention may be any gene of interest. As discussed below it will share homology with the fiNA. In particular it may be a homologous endogenous gene (HEgene) or a stably transformed homologous transgene (STgene, as with the stGFP used above).

More than one target gene (e.g. a gene family) may be targeted simultaneously provided that they all share homology with the fiNA.

As will be discussed in more detail hereinafter, in certain aspects of the invention the identity or phenotype of the gene may be unknown—and indeed TIGS may be used to identify it.

The "fiNA", which may be either DNA or RNA, may be synthetic (ie man made) or naturally occurring nucleic acid sequence which is a homolog of the target gene or it may be a copy of all or part of the target gene in sense or antisense orientation. It may be double or single stranded, for instance it may consist of antisense (double stranded) RNAs.

It should be stressed that, unlike RNA viral-based vectors used to effect gene silencing in the art (e.g Biosource Technologies, in WO 95/34668) the fiNA itself lacks sequences which permit movement from plant cell to plant cell, and optionally allow replication in the cytoplasm of plant cells (i.e. fiNA need not be capable of autonomous replication in the cell).

Unlike the amplicons of PCT/GB98/00442 (which may optionally lack such movement sequences) fiNA is not generated by a stably integrated transgene in the plant.

Thus the crucial elements of the fiNA which give the potential for signal initiation are that:

(i) it is foreign to the plant, or is at least recognised as being foreign, possibly after interacting with existing nucleic acids in the plant,
(ii) it shares homology with all or part of the target gene (coding or non-coding strand),
(iii) it cannot move from plant cell to plant cell (more particularly, does not comprise sequence encoding movement proteins or other pathogenicity proteins which would interfere with the signal) and optionally it cannot replicate autonomously in plant cell cytoplasm.

The term "foreign" is used broadly to indicate that the fiNA has been introduced into the cells of the plant or an ancestor thereof, possibly using recombinant DNA technology, but in any case by human intervention. Put another way fiNA will be non-naturally occurring in cells in to which it is introduced. For instance the fiNA may comprise a coding sequence of or derived from a particular type of plant cell or species or variety of plant, or virus, placed within the context of a plant cell of a different type or species or variety of plant. Alternatively the fiNA may be derived from the plant genome but is present in "unnatural" cellular or chromosomal locations, or lacks certain features of the authentic endogenous sequence (gene or transcript). A further possibility is for the fiNA to be placed within a cell in which it or a homolog is found naturally, but wherein the fiNA is linked and/or adjacent to nucleic acid which does not occur naturally within the cell, or cells of that type or species or variety of plant, such as operably linked to one or more regulatory sequences, such as a promoter sequence, for control of expression.

Regarding the "homology" of the fiNA, the complete sequence corresponding to the transcribed sequence need not be used to effect gene silencing, as is clear from the prior art studies (which albeit did not use fiNA as described herein or provide TIGS). For example fragments of sufficient length may be used. It is a routine matter for the person skilled in the art to screen fragments of various sizes and from various parts of the coding or non-coding sequence of the target gene to optimise the level of gene silencing, for instance using systems based on the GFP system described later. It may be advantageous to include the initiating methionine ATG codon of the target gene, and perhaps one or more nucleotides upstream of the initiating codon. A further possibility is to target a conserved sequence within a target gene, e.g. a sequence that is characteristic of one or more target genes in order to silence several genes which comprise the same or similar conserved sequence.

A fiNA may be 300 nucleotides or less, possibly about 200 nucleotides, or about 100 nucleotides. It may be possible to use oligonucleotides of much shorter lengths, 14–23 nucleotides. Longer fragments, and generally even longer than 300 nucleotides are preferable where possible if the fiNA is produced by transcription or if the short fragments are not protected from cytoplasmic nuclease activity.

It may be preferable that there is complete sequence identity between the fiNA and a relevant portion of the target sequence, although total complementarity or similarity of sequence is not essential. One or more nucleotides may differ in the targeting sequence from the target gene. Thus the fiNA of the present invention may correspond to the wild-type sequence of the target gene, or may be a mutant, derivative, variant or allele, by way of insertion, addition, deletion or substitution of one or more nucleotides, of such a sequence.

The fiNA need not include an open reading frame or specify an RNA that would be translatable. There may be a TIGS signal even where there is about 5%, 10%, 15%, 20% or 30% or more mismatch between the fiNA and the corresponding homologous target sequence. Sequence homology (or 'identity' or 'similarity'—the terms are used synonymously herein) may be assessed by any convenient method e.g. it may determined by the TBLASTN program, of Altschul et al. (1990) *J. Mol. Biol.* 215: 403–10, which is in standard use in the art.

Regarding translocation of the TIGS signal, as described above this is generated when the cells of the plant are transiently exposed to the fiNA, and the translocating tissues comprise, and preferably transcribe (though not necessarily express) the target gene or another 'resident gene' sharing homology with the target gene and the fiNA for the gene silencing signal to be transmitted through such tissues. However it may not be necessary for all of the translocating tissues to transcribe the gene—as shown in the Examples below, the signal may be 'relayed' between expressing cells.

The resident gene, which is discussed in more detail below, may be either endogenous or exogenous to the plant. The term 'homology' in relation to the resident gene is used in the same way as it is used in relation to the fiNA/target gene above. In this case the crucial element is that the homology be sufficient to allow signal generation and/or propagation. As described above the homology will preferably be at least 70%, more preferably at least 75%, more preferably at least 80%, more preferably at least 85%, more preferably at least 90% or most preferably more than 95%.

The advantage of using an STgene as a resident gene is that its transcription may be more readily controlled (if desired) than a target gene which is an HEgene, as is discussed in more detail in relation to facilitating signal propagation below.

The "transient exposure" of the second part of the plant to the fiNA may be achieved by any convenient method. Essentially the fiNA should be introduced directly or indirectly (e.g. exposure of a fiNA produced in the nucleus from locally present foreign nucleic acid) into the cytoplasm of cells of the second part of the plant.

Known methods of introducing nucleic acid into plant cells include use of a disarmed Ti-plasmid vector carried by Agrobacterium exploiting its natural gene transfer ability (EP-A-270355, EP-A-0116718, NAR 12(22) 8711–8721 (1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1–11.

Preferably fiNA is introduced by microprojectile bombardment with gold particles. Vacuum infiltration or injection of agrobacterium or direct uptake mediated by carborundum powder, whiskers (see Frame et al, Plant J 1994, 6: 941–948) or electroporation.

Various Embodiments Will Now Be Exemplified
Introduction of fiNA—Initiation of the Signal As described above fiNA may be introduced directly as naked DNA, or it may be transcribed from nucleic acid introduced into (but not stably integrated throughout) a plant. It should be stressed that although the fiNA must be located in the cytoplasm of the cell, there is no requirement that the fiNA be transcribed in the cell; thus there is no need for the fiNA to incorporate a promoter region in order to initiate the gene silencing signal or for it to be introduced into the cytoplasm via the nucleus.

In a further embodiment it may be possible to use a viral or other extrachromosomal expression vector (which may or may not include translation signals) e.g. a viral-based vector, encoding the fiNA, and a replicase, but lacking transmissive elements (e.g. movement proteins or other pathenogenicity proteins) which could inhibit the generation of a signal which can move beyond the infected parts of the plant, or be sustained within the plant after initial introduction. However viruses, particularly those which are transmissible, may be undesirable for other reasons e.g. safety, resistance etc.

In a further embodiment it may be achieved by transiently (e.g. locally) initiating the transcription of a fiNA-encoding sequence which is present in the cells, possibly the nucleus or the genome, of the second part of the plant.

This may be achieved by the use of Ti-based binary vectors (cf. use of the trGFP described below). Generally speaking, those skilled in the art are well able to construct vectors and design protocols for transient recombinant gene transcription. For further details see, for example, *Molecular Cloning: a Laboratory Manual:* 2nd edition, Sambrook et al, 1989, Cold Spring Harbor Laboratory Press.

Optionally transcription of the fiNA may be placed under the control of an activating agent, for instance using an inducible promoter.

The term "inducible" as applied to a promoter is well understood by those skilled in the art. In essence, transcription under the control of an inducible promoter is "switched on" or increased in response to an applied stimulus. The nature of the stimulus varies between promoters. Some inducible promoters cause little or undetectable levels of transcription (or no transcription) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

One example of an inducible promoter is the GST-II-27 gene promoter which has been shown to be induced by certain chemical compounds which can be applied to growing plants. The promoter is functional in both monocotyledons and dicotyledons. It can therefore be used to control gene expression in a variety of genetically modified plants, including field crops such as canola, sunflower, tobacco, sugarbeet, cotton; cereals such as wheat, barley, rice, maize, sorghum; fruit such as tomatoes, mangoes, peaches, apples, pears, strawberries, bananas, and melons; and vegetables such as carrot, lettuce, cabbage and onion. The GST-II-27 promoter is also suitable for use in a variety of tissues, including roots, leaves, stems and reproductive tissues. Other example inducible promoters are well known to those skilled in the art, the choice of which will be determined by the convenience of using the inducing agent in the particular application being carried out.

Another suitable promoter may be the DEX promoter (Plant Journal (1997) 11: 605–612).

In this embodiment the activating agent can be applied locally to one or more regions of the plant in which the fiNA-encoding construct has been introduced (the 'second part') in order to achieve the remote silencing of other ('first part').

In a most preferred aspect, the fiNA may be introduced as a construct corresponding to a truncated 'amplicon' of GB 98/00442. This will generally comprise:

(i) a plant promoter (ii) a nucleic acid sequence operably linked to that promoter, said sequence encoding an RNA-dependent replicase, and further encoding fiNA, which is itself operably linked to a sub-genomic promoter capable of being recognised by said replicase, such that the fiNA is capable of autonomous cytoplasmic replication, with the proviso that the nucleic acid sequence does not encode active viral movement proteins (plus optionally pathogenicity proteins) which would otherwise inhibit the TIGS signal from spreading systemically in the plant into which the construct is introduced.

By "replicase" is meant, where appropriate, all the required components to give replicase function. The construct does not encode "active movement proteins" in the sense that, although a movement proteins may be encoded, they are not functional e.g. because one or more has been deleted or modified.

Propagation and Maintenance of the Signal Through the Plant

The advantage of achieving systemic gene silencing using transient activation or introduction of fiNA in a localised area (e.g. by application of a specific agent) is that there is no requirement for the inducing agent of fiNA to be translocated within the tissues of the plant or be applied to all parts of the plant. Once initiated the signal can induce gene silencing in remote parts of the plant. This gene silencing is stable and persists even after the fiNA ahs been removed.

By "remote" is meant the first and second parts of the plant are spatially separated, although obviously connected via the plant tissues. It may be advantageous if the first part of the plant is above the level of the second, or if the route corresponds to the 'source-sink' movement of photosynthetic products from regions in which they are concentrated to regions of use. The observations described in the Examples suggest that signal movement mimics in some respects viral or viral-vector movement. It should be stressed, however, that neither the signal of the present invention, nor the fiNA used to initiate it, are viruses, for instance mobile, cytoplasmatically replicable vectors.

It should also be stressed that the part of the plant in which the target gene is to be silenced may encompass all, or almost all, of that part of the plant which is not directly exposed to the fiNA i.e. systemic silencing.

Thus in one embodiment of this aspect, the target gene is silenced systemically in the plant tissues i.e. in the first and second parts of the plant and the tissues between them, (cf. the stGFP described below).

It may not be necessary for all the cells in these tissues to transcribe the target gene, as detailed in the Examples.

Alternatively, some or all of the cells of the connecting plant tissues will comprise a resident gene, the transcription (though not necessarily expression) facilitates the propagation of the signal.

By "resident gene" is meant a gene (endogenous or exogenous) which is homologous to the target gene and homologous to the fiNA such as to facilitate transduction of the TIGS signal.

Thus in a second embodiment of this aspect, the target gene is transcribed only in a second, remote, part of the plant (e.g. it is expressed in a tissue specific manner), but a resident gene which is homologous to the target gene is present and preferably transcribed in the plant tissues in the second part of the plant and/or the tissues between the first and second parts of the plant. Presence or preferably transcription of this resident gene may thus serve to cause or allow signal propagation.

This embodiment permits control of tissue specific target genes. The resident gene serves to assist systemic spread of the signal. The systemic spread of the signal can thus be controlled at an additional level to the direct control of the fiNA exposure, providing further temporal and spatial control over gene silencing:

By regulating the transcription of the resident gene in the cells carrying the TIGs signal, it will be possible to determine whether gene silencing in the first part of the plant is activated effectively, or to affect the tissue specificity of gene silencing.

Transcription of a resident (STgene) may be altered by use of an inducible promoter, such as is described above in relation to the fiNA.

It will be apparent from the foregoing that the invention embraces methods of controlling gene silencing in plants by manipulating the presence or transcription of the fiNA or the propagation of the signal. e.g. by controlling the presence or absence of an activating agent which induces transcription of a resident gene. Physical methods for manipulating the resident gene expression are also envisaged. For instance grafts of tissue between the different parts of the plant which are either permissive (i.e. contain cells having the resident gene) or non-permissive (cells don't have the resident gene) can be used to control translocation of the signal.

Selected Applications for TIGS

In embodiments of the present invention which have been experimentally exemplified as described below for illustrative and non-limiting purposes only, the transiently introduced gene encoding the fiNA that determined the target of gene silencing was the gene encoding the jellyfish green fluorescent protein GFP (Chalfie et al. (1994) *Science* 263: 802–805). This was used to silence a stably integrated GFP transgene.

Any other ST- or HEgene of a plant, or STgene of animal, fungal, bacterial or viral origin may be a target gene provided that the fiNA contains a corresponding homologous sequence.

In one aspect of the present invention, the target gene may be of unknown phenotype, in which case the TIGS system may be employed to analyse the phenotype by generating a systemic (or widespread) null (or nearly null) phenotype.

Thus a further aspect of the invention comprises a method of characterising a target gene comprising the steps of:

(a) silencing the target gene in a part or at a certain development stage of the plant using the TIGS system described above, (b) observing the phenotype of the part of the plant in which or when the target gene has been silenced.

Preferably the gene is silenced systemically. Generally the observation will be contrasted with a plant wherein the target gene is being expressed in order to characterise (i.e. establish one or more phenotypic characteristics of) the gene.

There are several advantages of the current method over alternative methods in which the targeted gene is inactivated by insertional or other mutagenic procedures or in which gene silencing is uncontrolled. The advantage over mutagenic procedures applies when there is more than one homologous gene carrying out the role of the target gene. Mutagenic procedures will not normally reveal a phenotype in that situation. A second situation where the current invention has advantage over both mutagenic and unregulated gene silencing procedures applies when the target gene has a lethal phenotype. The controllable attribute of the gene silencing will allow the phenotype of such genes to be investigated and exploited more efficiently than using the alternative methods available prior to the disclosure of the current invention.

This aspect is particularly useful given the significant amount of sequence data currently being generated in genomics projects which is unassigned in terms of function or phenotype. Thus even if the gene exerts its effects only in particular tissues, this may be detectable without having to ensure that a virus has permeated the entire plant (as in Biosource Technologies, WO 95/34668).

Nor, for the identification of HE genes, would it be necessary to try and generate a transgenic plant in which gene silencing is already activated to observe the effect.

In a further aspect there is disclosed a method of altering the phenotype of a plant comprising use of the TIGS method.

Traits for which it may be desirable to change the phenotype include the following: colour; disease or pest resistance; ripening potential; male sterility.

For instance male sterile plants are required for production of hybrid seed. To propagate the male sterile lines it is necessary to restore male fertility. In the examples in which male sterility is induced by a transgene it would be possible to restore male fertility by controlled silencing of the transgene using the approach described above.

Many genes have multiple roles in development. They may be required, for example, in embryo development and in the development of organs or tissues in the mature plant. Obviously it would not be possible to silence these genes unless the silencing system could be controlled so that it is not active in embryo development. The system described here could be used to provide that control.

Other traits will occur to those skilled in the art. In each case the only necessity is that sufficient is known about the target gene(s) to devise suitable fiNA, which may of course be optimised without burden to achieve the desired effect. If the target gene is not expressed systemically, then it may be necessary to produce a transgenic plant wherein a resident STgene is transcribed systemically in order to allow signal propagation. The fiNA can then be used to initiate the signal.

The production of transgenic plants is now very well known to those skilled in the art, as evidenced by the various reported methods some of which are recorded in non-prior published GB patent application 9703146.2 in the name of John Innes Centre Innovations Limited, the content of which is incorporated herein by reference.

In a further aspect of the present invention there is disclosed a method for producing a systemic gene silencing signaling agent in a plant, which is capable of silencing a target gene comprising causing or allowing the transient exposure of a part of the plant expressing said target gene or a homolog thereof to a fiNA.

The systemic gene silencing signaling agent is characterised in that it (a) comprises nucleic acid, (b) is capable of mediating sequence-specific gene silencing of a target gene, (c) it is obtainable by transient exposure of a plant cell transcribing said target gene or a homolog thereof to a fiNA, (d) is capable of moving between a first and second part of the plant, said parts being connected by cells comprising, and preferably transcribing said target gene or a homolog thereof, which movement is inhibited my movement or pathogenicity proteins as discussed above.

The various nucleic acids of the present invention may be provided isolated and/or purified (i.e. from their natural environment), in substantially pure or homogeneous form, or free or substantially free of other nucleic acid. Nucleic acid according to the present invention may be wholly or partially synthetic. The term "isolate" encompasses all these possibilities.

Also embraced by the present invention is a transgenic plant comprising a target gene which has been systemically silenced using TIGS.

The present invention may be used in plants such as crop plants, including cereals and pulses, maize, wheat, potatoes, tapioca, rice, sorgum, millet, cassava, barley, pea and other root, tuber or seed crops. Important seed crops are oil seed rape, sugar beet, maize, sunflower, soybean and sorghum. Horticultural plants to which the present invention may be applied may include lettuce, endive and vegetable brassicas including cabbage, broccoli and cauliflower, and carnations and geraniums. The present invention may be applied to tobacco, cucurbits, carrot, strawberry, sunflower, tomato, pepper, chrysanthemum, poplar, eucalyptus and pine.

The present invention will now be illustrated and exemplified with reference to experimental results and the accompanying Figures. Further aspects and embodiments of the present invention, and modifications of those disclosed herein, will be apparent to those skilled in the art. All documents mentioned anywhere herein are incorporated by reference.

FIGURES

FIGS. 1A–C. Transaene and Viral Constructs

FIG. 1a T-DNA from pBin-35S-mGFP5 used for *Nicotiana benthamiana* stable transformation (pnos: nos promoter, tnos: nos terminator, 35S: CaMV-35S promoter, RB: right border, LB: left border). This is the STgene construct.

FIG. 1b T-DNAs from various binary vectors carried by *Agrobacte.rium tumefaciens* strain LBA4404 used for leaf infiltrations (OCS: octopine synthase terminator, BaR: BASTA resistance gene). These are TRgene constructs. lacZ: multiple cloning site, inserted for cloning facilities.

FIG. 1c Structures of PVX-GUS[17] and PVX-GFP[16]. Expression of the inserted marker genes is controlled by a duplicated coat protein (CP) promoter (shaded boxes). Other abbreviations are RdRp: RNA dependent RNA polymerase, and 25K, 12K, 8K: cell-to-cell movement proteins. These constructs were used, inter alia, in determining whether gene silencing was pre- or post-transcriptional.

FIGS. 2A–L. Expression of GUS and GFP reporter genes in *N. benthamiana*

These images were all produced under UV illumination except for the bottom panels of E and F and panels I–L that show leaves stained for GUS activity[24]. The method and abbreviations are described in more detail in Example 1. Depending on the exposure time and the source of UV, GFP appears green or yellow. In the absence of GFP the chlorophyllous plant tissue appears red.

(FIG. 2a) A leaf of a stably integrated GFP homogene (stGFP) plant (FIG. 2b) A leaf of a non-transgenic (not) nt plant.

(FIGS. 2c–d) stGFP plants infiltrated 18 d previously with a culture of the NPT:GUS:GFP strain of *A. tumefaciens*, prepared in the presence (c) or in the absence (d) of acetosyringone; the arrows indicate the infiltrated leaves.

(FIGS. 2e–f) Expression of trGFP (top panel) and GUS (bottom panel) in leaves of an nt plant (e) or an stGFP plant (f) that had been infiltrated with the NPT:GUS:GFP strain of *A. tumefaciens* 2 days previously. The arrow in (e) indicates the zone of stGFP suppression at the edge of the infiltrated zone where A line of red fluorescent tissue is observed.

(FIG. 2g) Close-up view of an axillary shoot emerging from one of the three fully expanded leaves of the plant presented in (c). Leaves on these axillary shoots always show very strong stGFP suppression. The diffuse patches of residual expression of stGFP fade when these leaves expand. Some of the smaller leaflets on the axillary shoots as shown in this panel (arrow) are uniformly red.

(FIG. 2h) UV illumination of upper leaves emerging from the main stem of A stGFP plant infiltrated 18 days previously with water (left), or with the NPT:GUS:GFP strain of *A. tumefaciens*. (middle and right).

(FIG. 2i) Leaves shown in (h) were stained for GUS activity (FIG. 2j) A leaf infiltrated with an NPT:GUS:GFP strain of *A. tumefaciens* as an internal control for the histochemical GUS staining shown in (i).

(FIGS. 2k–l) PVX-GUS foci observed on A systemic leaf of an stGFP plant infiltrated with either the NPT:GUS:GFP strain of *A. tumefaciens* (k) or with water (l). Leaves were inoculated with PVX-GUS and collected after 5 days for GUS staining. When leaves were collected later than 5 days post-inoculation, the GUS foci had spread to the veins, indicating a potential for systemic spread of PVX-GUS independently of stGFP silencing.

Figure 3:
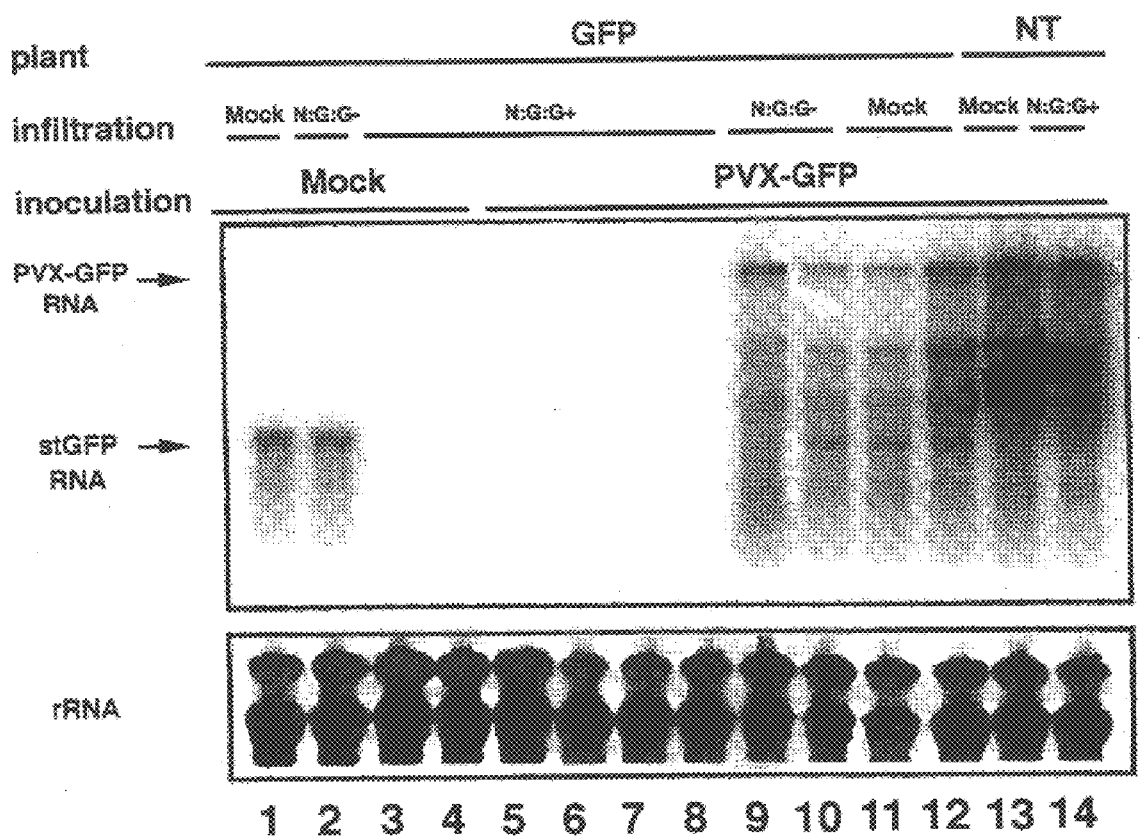

FIG. 3. Northern analysis of stGFP and PVX-GFP RNA. stGFP plants (GFP) or nt plants (NT) were infiltrated with either water (Mock), or the NPT:GUS:GFP strain of *A. tumefaciens* previously induced with acetosyringone (N:G:G)-X(N:G:G-) indicates that the culture was not previously induced. After 20 d, two upper leaves were inoculated with water (Mock) or PVX-GFP. 5 d after virus inoculation, total RNA was extracted from one of the two inoculated leaves and northern analysis on 10 μg of RNA was carried out to detect accumulation of the stGFP RNA and PVX-GFP RNA (indicated on the left side of the upper panel). The heterodisperse RNA species in tracks 9–14 represent sub-genomic and degraded RNA species and are typical of PVX RNA samples of inoculated leaves. The lower panel shows probing of the northern blot with an rRNA probe to confirm equal loadings of RNA.

In Figure legends 4 to 7, the intGFP refers to stably integrated GFP, while epiGFP refers to infiltrated sequence.

Figure 4:
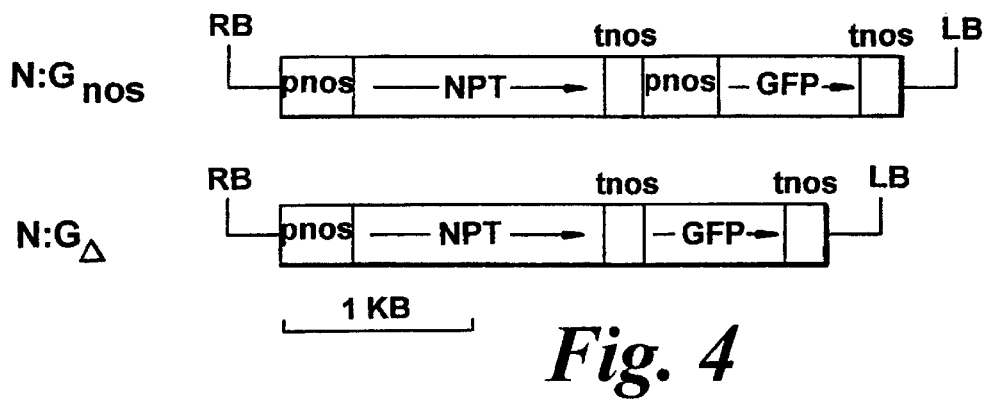

FIG. 4. Constructs used in Example 13

The T-DNA constructs used for Agrobacterium infiltrations are derived from the N:G:G construct. The 35S promoter controlling the GFP gene has been replaced by the nos promoter in the N:Gnos construct, and has been deleted in the N:GΔ construct.

Figure 5:
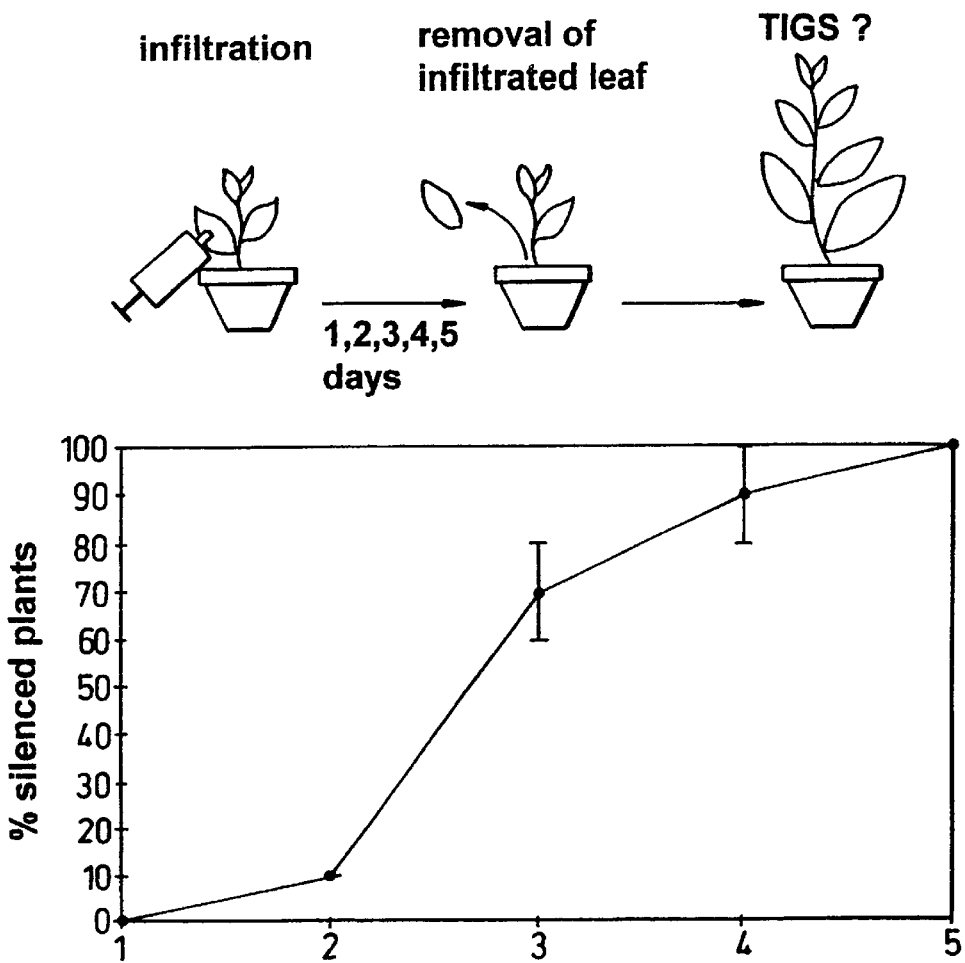

FIG. 5. Kinetics of translocation of the TIGS signal

The top diagram illustrates the order of events described below. One leaf of intGFP plant was infiltrated with the N:G:G strain of *A. tumefaciens* (previously induced with acetosyringone), and subsequently removed 1,2,3,4 or 5 days after infiltration. The percentage of plants undergoing TIGS after removal of the infiltrated leaf was then assessed under UV illumination. Each dot on the diagram represents the average percentage obtained from 30 individual plants infiltrated at the same time (see Example 14).

Figures 6A, 6B:
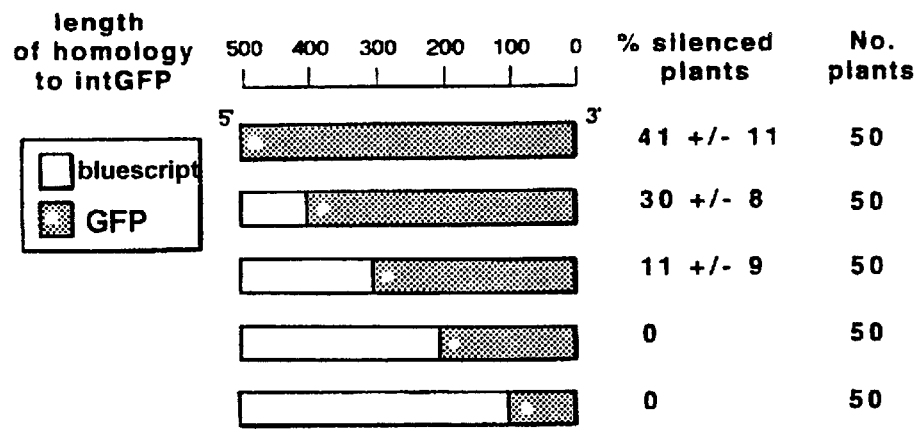

FIGS. 6A and B. Biolistic activation of TIGS (FIG. 6A) DNA constructs tested for biolistic activation of TIGS. The pUC35S-GFP plasmid contains the 35S-GFP expression cassette from pBin35S-GFP (FIG. 1). The GFP plasmid contains only the full-length GFP open reading frame from pBin35S-GFP cloned as a BamHI-SalI restriction fragment in pUC19. The ..P and G.. DNA constructs are linear, PCR-amplified fragments of the GFP open reading frame and are respectively 348 and 453 bp long. Equal amounts of each construct were bombarded (see Experimental Procedures and Example 16).

(FIG. 6B) Effect of the length of homology between epiGFP and intGFP on biolistic activation of TIGS. The intGFP seedlings were bombarded with a series of PCR-amplified fragments sharing a similar physical length but harbouring 3' terminal fragments of GFP cDNA of varying length. These fragments were amplified from a pBluescript vector containing the full-length GFP open reading frame by using one vector-specific primer and one GFP-specific primer. The white dot on the diagram represents the 5' end of the GFP open reading frame. Equal amounts of each construct were bombarded (See Experimental Procedures and Example 16).

FIGS. 7A and 7B. TIGS requires an interaction of epiGFP and intGFP

See Example 17.

(FIG. 7A) Bombarded epiGFP and inoculated viral constructs. The ..P and GF. DNA constructs are derivatives of the GFP construct described in FIG. 5A. PVX-GF and PVX-P are PVX vectors carrying the GF. and ..P restriction fragments of the GFP open reading frame, respectively.

(FIG. 7B) Northern analysis of intGFP and PVX-GF/GFP RNAs. The top diagram illustrates the order of events described below. First intGFP seedlings or non-transformed plants (NT) were bombarded with either uncoated gold particles (-) or gold particles coated with either the GFP or the ..P construct. After 21 days, two upper leaves were inoculated with either water (Mock), PVX-GFP or PVX-GF. The plants bombarded with GFP or derivatives exhibiting TIGS were selected for the virus inoculation. Five days after virus inoculation, total RNA was extracted from one of the two inoculated upper leaves and Northern analysis of 10 μg of RNA was carried out to detect accumulation of the intGFP and PVX-GF/GFP RNA (indicated on the left side of the upper panel).

Figure 8A:
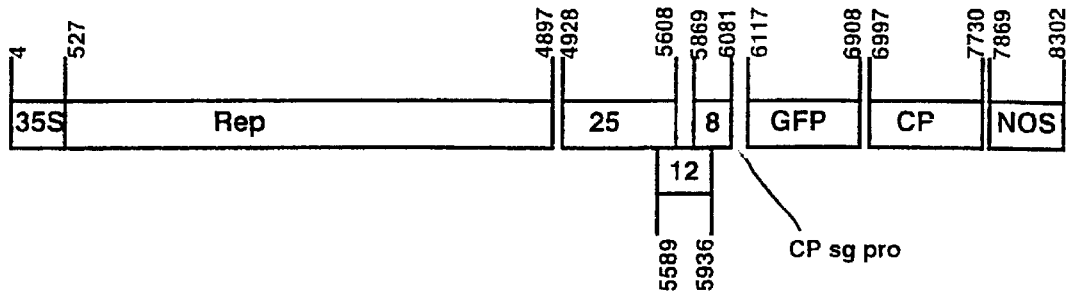
Figure 8B:
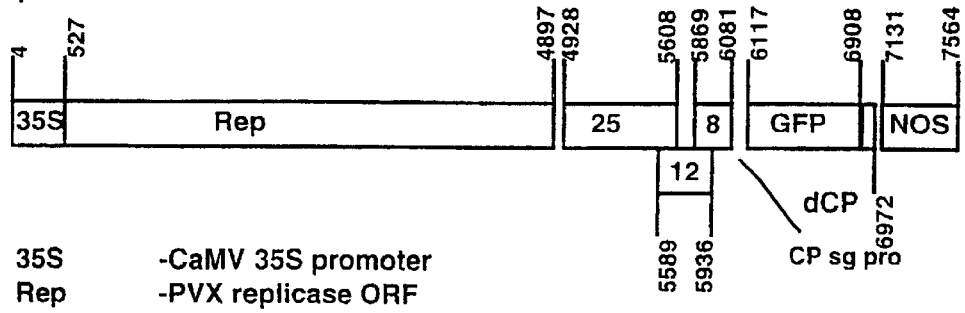
Figure 9A:
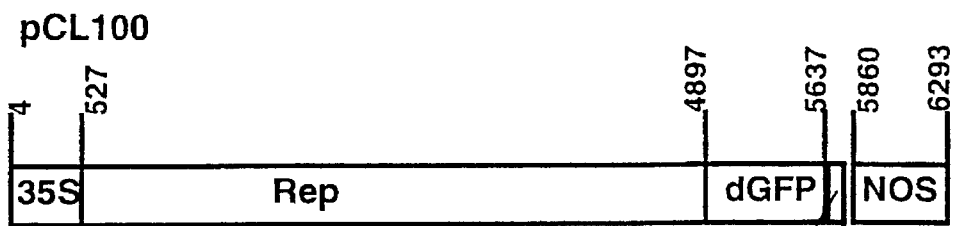
Figure 9B:
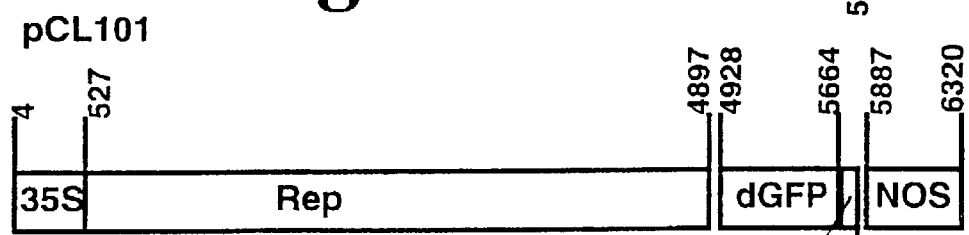
Figure 9C:
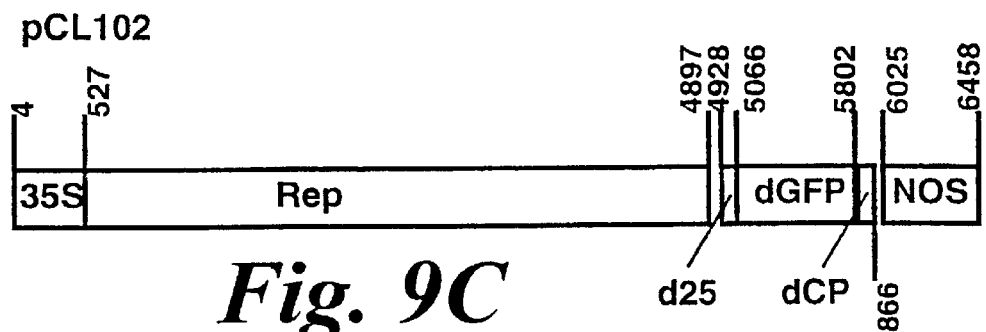
Figure 9D:
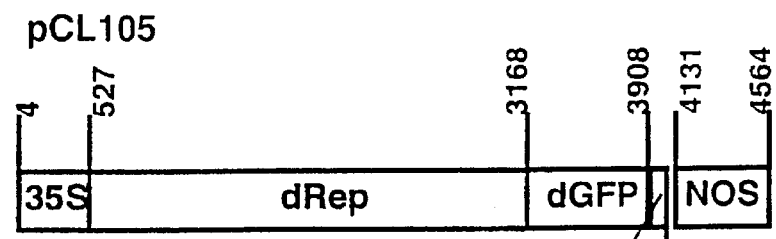
Figure 9E:
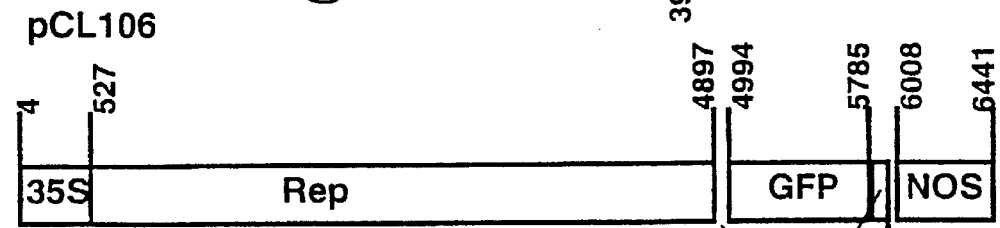
Figure 9F:
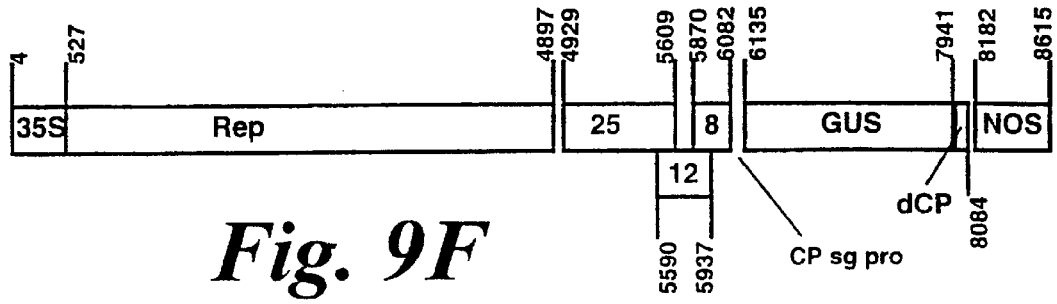
Figure 9G:
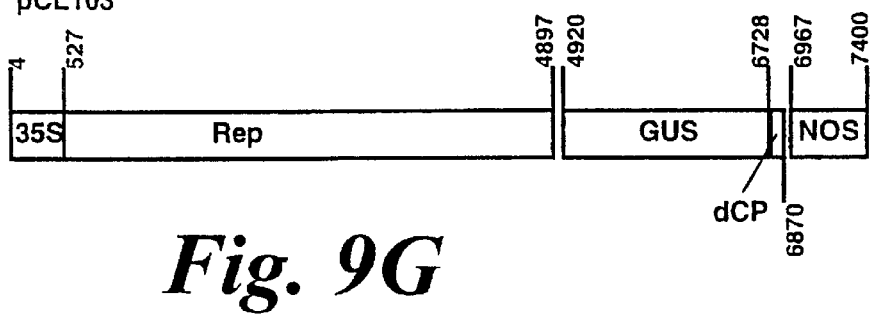
Figure 9H:
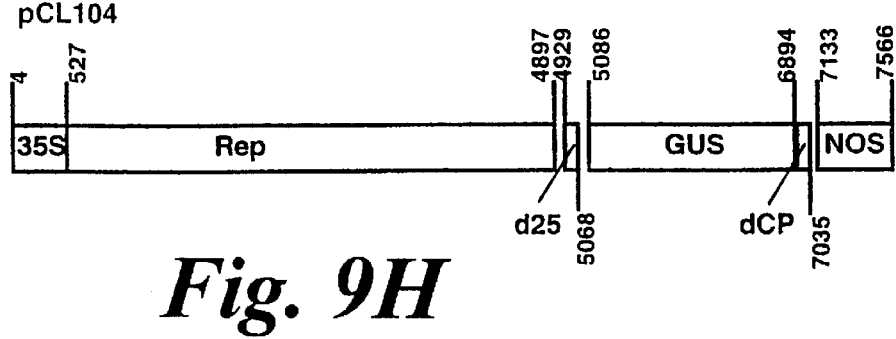

FIGS. 8A and 8B: pPVX209 and pPVX210A

As described in Example 19, the CP was deleted from pPVX209 [FIG. 8 (A)] to create, pPVX210A [FIG. 8 (B)]. The sequence is numbered from the 35S promoter, with the SacI site immediately upstream of the promoter being numered as nucleotide 4.

FIGS. 9A–9H: pCL-vectors and progenitor construct

After eliminating the TGB (triple gene block) tagged PCR fragments amplified from pPVX210A were re-inserted to restore replicase function. Shown are (FIG. 9a) pCL100; (FIG. 9b) pCL101; (FIG. 9c) pCL102; (FIG. 9d) pCL105 (includes a 1729 bp deletion in the replicase) (FIG. 9e) pCL106 (includes a PCR-fragment from pPVX210A to restore GFP function and enhance the production of sub genomic RNA); (FIG. 9f) progenitor construct pA500 [see Table 2; Example 19; (FIG. 9g) pCL103; (FIG. 9h) pCL104. See FIG. 8 for explanation of terms.

FIGS. 11A–11F: Positive strand sequences of constructs

Restriction sites used in cloning are underlined and labelled in grey. 'Xxxx' indicates the ligated SalI/XhoI half sites. Abridged parts of the sequences are labelled in tildes (''). The 144 underlined bases represent the duplicated CP promoter region which together with the downstream GFP 5' end was inserted into pCL100 to create pCL106. Bases in lower case indicate non-viral sequence introduced by PCR primers used in cloning. Sequences confirmed after the respective cloning step are double underlinded, single bp exchanges or deviations not unambiguously falsified by examining the sequencing raw data are in minor case italics. Spacing for the CP deletion is condensed in TGB deletion constructs.

(a) pPVX209 (1-762 nt) SEQ ID NOS: 14, 15 and 16;
(b) pPVX210A (10024 nt) SEQ ID NOS 14, 15, 16, 17 and 18;
(c) pCL100 (8753 nt) SEQ ID NOS: 19, 20 and 21;
(d) PCL102 (8918 nt) SEQ ID NOS: 22, 20 and 21;
(e) pCL101 (8780 nt) SEQ ID NOS: 23, 20, 21;
(f) pCL106 (8901 nt) SEQ ID NOS: 24, 20 and 21

EXAMPLES

General Methods—Examples 1 to 12
Plant Transformation

Four independent lines of *Nicotiana benthamiana* plants carrying the GFP transgene (stGFP plants) were generated by the *A. tumefaciens*-mediated leaf disk transformation method[22]. For transformation, we used the disarmed Agrobacterium strain GV-3101 containing the binary vector pBin-35S-mGFP5[23]. Restriction digestion and Southern analysis showed that each line harbours a single T-DNA integration site, consistent with the observed 3:1 segregation of the expression of GFP in the R1 generation. In all cases, this single locus is associated with one intact copy of the GFP transgene. Northern analysis showed comparable high levels of GFP mRNA in these four independent lines. All stGFP plants used in this work were homozygous, selfed F1 progeny of the primary transformants.

Infiltration of Agrobacterium and the Selective Enrichment Assay

Infiltration of Agrobacterium cultures for transient expression was based on a previously-described method[13]. First, the constructs shown in FIG. 1b were transferred to *A.tumefaciens* GV3101 by triparental mating and the strains were plated on minA medium. A single colony was inoculated into 5 ml LB medium supplemented with the appropriate antibiotics, and grown at 28° C. for 48 hours. One ml of the culture was transferred to 100 ml LB with 10 mM MES pH 5.6 and 20 μM acetosyringone, and grown at 28° C. for 16 hours. The bacteria (OD600=1) were spun down, suspended in 50 ml 10 mM $MgCl_2$ and kept at room temperature for 3 hours. The infiltration, performed with a 2 ml syringe, was to one or two expanded leaves of 3 week-old seedlings. The infiltrated leaves were then sealed in a small plastic bag for two days. Seedlings were maintained in A glasshouse between 20° C. and 25° C. Artificial illumination was used, if necessary, to provide A day length of 16 hours or more.

The selective enrichment assay for Agrobacterium was as described[19]. Using this procedure a single isolated Agrobacterium cell mixed with 0.1 g of tobacco tissue could be enriched to the late exponential phase after 3 days of incubation.

General Procedures

PVX-GFP and PVX-GUS inocula were sap extracts of plants (*Nicotiana clevelandii*) infected with in vitro transcripts of the corresponding cDNA clonesl[16,17]. RNA isolation and Northern analysis were done as described[17]. The probe used for hybridization was a $^{32}P$-labelled cDNA corresponding to the entire GFP open reading frame. Histochemical staining of plant material for GUS activity was performed according to the method of Jefferson[24].

General Methods—Examples 13–19
These were as Above Except
Infiltration of Agrobacterium Infiltration of *A. tumefaciens* was based on a previously-described method (English et al., 1997). The constructs shown in FIG. 4 were transferred to *A. tumefaciens* (strain GV3101, unless otherwise stated) by triparental mating or electroporation and the strains were plated on mina medium. Procedure was as described above.

Grafting Procedure

Non-transformed and transgenic *N. benthamiana* plants were grown about 1 month before grafting. The stocks were beheaded 10–15 cm from the soil and wedge-grafting was performed with scions of similar age. The graft junction was then fastened and protected from desiccation by Parafilm.

During the first week after grafting, plants were covered with a plastic bag to maintain high humidity conditions.

Seedling Bombardment

*N. benthamiana* seeds were sterilised with 0.25% sodium hypochlorite for 15 min and rinsed 3 times with sterile water. Seeds were germinated for 7–10 days on MSR6 medium. One day before bombardment the seedlings in groups of 10–12 were transferred onto fresh MSR6 medium distributed over a 3.2 cm2 target area. DNA coating and particle bombardment were carried out as described previously (Christou et al., 1991). Each group of 10 seedlings was bombarded twice with 163 ml of gold particles coated with 326 ng of DNA and accelerated at 12 Kv. Two weeks after bombardment seedlings were transferred to a glasshouse between 20° C. and 25° C. Artificial illumination was used, if necessary, to provide a day length of 16 hours or more.

In Vitro Propagation

*N. benthamiana* leaves were harvested from greenhouse-grown plants. Leaves were sterilised with 0.25% (w/v) sodium hypochlorite for five minutes and rinsed three times with sterile distilled water. Leaf disks were aseptically plated onto MSR6 medium (Vain et al., 1998) complemented with 1 mg/l 6-Benzylaminopurine and 0.1 mg/l (-Naphthaleneacetic acid. Culture was conducted in 2 cm deep Petri dish sealed with Micropore( tape, at 23 (C. and under a 16 hours photoperiod. Leaves were subsequently transferred at 15 day intervals onto fresh medium. After 4 to 6 weeks the regenerated shoots were dissected and rooted onto MSR6 medium.

GFP Imaging

Visual detection of GFP fluorescence in whole plant was performed using a 100 W hand-held long-wave ultraviolet lamp (UV products, Upland Calif. 91786, Black Ray model B 100AP). Plants were photographed with a Kodak Ektachrome Panther (400 ASA) film through a Wratten 8 filter. Exposure times varied up to 70 sec depending on the intensity of the fluorescence and the distance of the camera and lamp from the plant. Observation of explants cultured in vitro was carried out using a MZ12 Leica dissecting microscope coupled to an epifluorescent module. Photographs were taken using Kodak Ektachrome Panther (400 ASA) film. Confocal microscopy was performed under a Leica DMR module coupled to a Leica TCS-NT system. A 100 mW Argon ion laser was used to produce blue excitation light at 488 nm (emission filter 522 nm). Using these filter combinations, background autofluorescence from the samples was removed. Individual images were stored on optical disc.

Construction of PVX Derivatives and In Vitro Transcription

PVX-GFP has been described previously (Baulcombe et al., 1995). PVX-GF was made by replacing the original GFP insert in the PVX vector pTXS-GFP (Baulcombe et al., 1995) by the mGFP5 insert from pBin-35S-mGFP5 (Haseloff et al., 1997) and by removing the 354 bp fragment between a ClaI site (position 465 within the GFP5 coding sequence) and a SalI site at the 3' end of GFP5 (position 818). PVX-P was made by inserting a ClaI-SalI restriction fragment from GFP5 into the PVX vector pP2C2S (Baulcombe et al., 1995). Viral inocula were sap extracts of plants (*N. clevelandii*) infected with in vitro transcripts (Chapman et al., 1992) of the corresponding cDNA clones.

Agroinfiltrated and Bombarded epiGFP Constructs

The N:G:G binary vector (FIG. 1) is based on pBIN 35S:GFP4 (Haseloff et al., 1997) in which the LacZ polylinker from pUC19 has been inserted in the HindIII blunted restriction site located upstream from the 35S promoter of GFP4. A 35S-GUS expression cassette from pSLJ4D4 (Jones et al., 1992) was then inserted in the LacZ polylinker as a HindIII-EcoRI restriction fragment. The N:Gnos and N:GΔ constructs (FIG. 4) are derived from pBin 35S:GFP4 by a BamHI-HindIII restriction, followed by blunt ending (Klenow) and religation. N:Gnos was obtained by removal of the 35S promoter by a BamHI-HindIII restriction, followed by Klenow DNA filling and insertion of the nos promoter. The pUC35S-GFP construct (FIG. 6) was obtained by inserting the 35 S:GfP4 expression cassette from pBIN 35S:GFP4 (HindIII-EcoRI restriction fragment) in pUC19. The GFP construct was obtained by inserting the full-length GFP open reading frame from pBIN 35S:GFP4 (BamHI-SAcI restriction fragment) in pUC19 (Yanisch-Perron et al., 1985). The "G.." fragment (FIG. 6) was PCR-amplified from PBIN 35S:GFP5 (Haseloff et al., 1997) using primers GGATCCAAGGAGATATAACAA (SEQ ID NO: 1) and AAATCGATTCCCTTAAGCTCG (SEQ ID NO: 2) (pos1 and pos453 in the GFP5 cDNA respectively). The "..P" fragment (FIG. 6) was PCR-amplified from pBIN 35S:GFP5 using primers AGCTTAAGGGAATCGAT (SEQ ID NO: 3) and CTTAGAGTTCGTCATGTTTGT (SEQ ID NO: 4) (pos 454 and pos 813 in the GF5 cDNA, respectively). The series of PCR amplified fragments used for the study of the effect of the length of homology between epiGFP and intGFP (FIG. 6B) was obtained from pBluescript in which the complete GFP5 cDNA was inserted as a BamHI-SacI restriction fragment. Primer combinations used for each amplification are: (AGCTTAAGGGAATCGAT (SEQ ID NO: 3)-TTGTGGCCGAGGATGTTT (SEQ ID NO: 5); (AAATCGATCCCTTAAGCTCG (SEQ ID NO: 6)-GGGTAACGCCAGGGTTTTCC (SEQ ID NO:7); (AGTAGTGACAAGTGTTGGCC (SEQ ID NO: 8)-AGCGGGCGCTAGGGCGCT (SEQ ID NO 9); (TGACAGAAAATTTGTGCCCATT (SEQ ID NO: 10)-GTAAAGCACTAAATCGGAACC(SEQ ID NO: 11); (TTGGGACAACTCCAGTGAAAA (SEQ ID NO: 12)-CCACTACGTGAACCATCAC (SEQ ID NO: 13). The ...P and GF. Constructs are respectively linear ClaI-SAlI and BamHI-ClaI restriction fragments from the GFP construct described above.

General Procedures

RNA isolation and Northern analysis were done as described (Mueller et al., 1995). The probe used for hybridisation was a 32P-labelled cDNA corresponding to the entire GFP open reading frame. Histochemical staining of plant material for GUS activity was performed using standard procedures (Jefferson, 1987).

Example 1

The Gene Silencing Signal Imposes Remote Silencing

To develop a reproducible system for activation of gene silencing we have used transient expression of silencer transgenes in *Nicotiana benthamiana*. The target of gene silencing (FIG. 1a) in these experiments encodes the jellyfish green fluorescent protein (GFP)[11] that can be monitored non-invasively: leaves of transgenic GFP plants appear green under UV light (FIG. 2a) whereas non transgenic (nt) leaves appear red due to chlorophyll fluorescence (FIG. 2b). To deliver silencer transgenes, we infiltrated leaves[12,13] of *N. benthamiana* with strains of *Agrobacterium tumefaciens* carrying various binary Ti plasmid vectors (FIG. 1b), including one with a GFP reporter gene. We refer to the stably integrated and transiently expressed GFP transgenes as stGFP and trGFP, respectively.

At 2 days post-infiltration with the NPT:GUS:GFP strain of *A. tumefaciens* (FIG. 1B) there was expression of both the GUS and the trGFP reporter genes in the infiltrated tissues (FIGS. 2e, 2f). In the stGFP transgenic lines (FIG. 2f) the strong green fluorescence due to the trGFP was superimposed over a weaker background fluorescence from the stGFP. However, at the edge of the infiltrated zone there was a thin line of red fluorescent tissue (FIG. 2f) indicating that stGFP expression had been suppressed.

Although the zone of stGFP suppression did not spread further within the infiltrated leaf, by 18 days post-infiltration there was suppression of stGFP in the upper leaves (FIG. 2c) of the NPT:GUS:GFP infiltrated plant. This effect was most pronounced in the stem and leaves that were directly above the infiltrated leaf and in the tissues surrounding the veins (FIG. 2c, 2h). In leaves of the axillary shoots (FIG. 2g) and in some uppermost leaves (FIG. 2h) there was complete suppression of green fluorescence due to stGFP. The time-course of stGFP suppression and its pattern of spread through the vegetative parts of the infiltrated plants were consistently observed in 5 independent experiments involving 20 plants of each of 4 independent stGFP lines.

Example 2

The Gene Silencing Signal is Sequence Specific

There was no suppression of stGFP when the plants were infiltrated with the NPT:GUS, GUS:BAR or empty vector strains of A. tumefaciens (FIG. 1b). If the suppression had been caused by the infiltration process these control strains would have caused suppression of stGFP. Similarly, if the 35S promoter or nos terminator components of the trGFP are involved, there would have been suppression of stGFP following infiltration with the NPT:GUS and GUS:BAR strains (FIG. 1b): these constructs have both 35S promoters and nos terminators. Therefore, the systemic suppression of stGFP is a sequence-specific effect based on the common presence of GFP coding sequences in stGFP and trGFP.

Example 3

The Gene Silencing Signal Requires Uptake of the Transgene Coding for the fiNA

Figure 2:
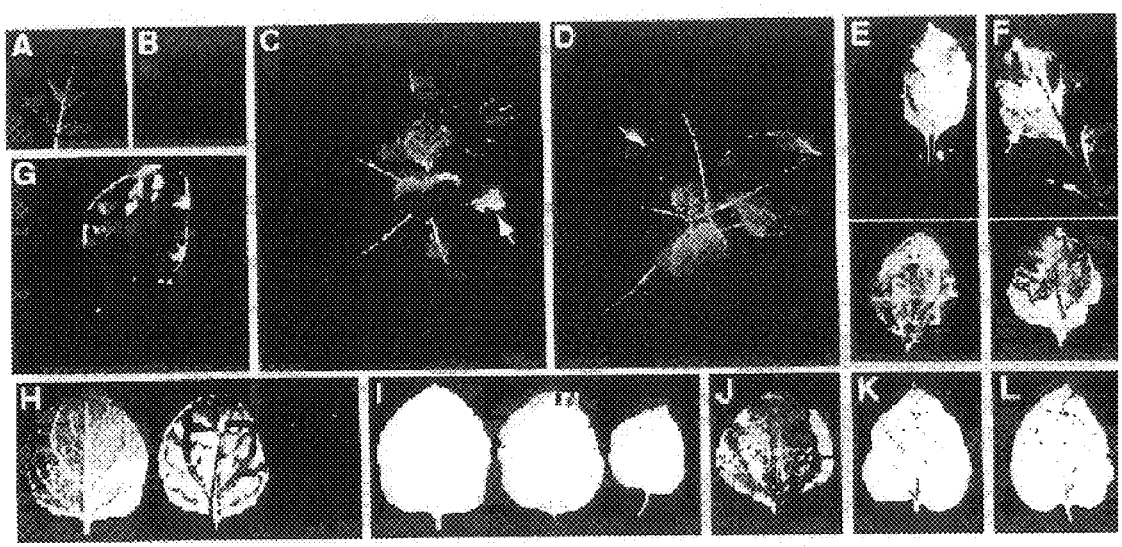

The A. tumefaciens cultures used in these experiments contained acetosyringone as an inducer of virulence (Vir) functions[4]. In the absence of Vir gene expression there is no transfer of T-DNA (between the right and left borders; FIG. 1b) from the Ti plasmid into the plant cell. Consequently, when leaves of nt N. benthamiana were infiltrated with the NPT:GUS:GFP strain of A. tumefaciens incubated without acetosyringone, there was no expression of GUS or trGFP at 2 days post-infiltration. In addition, there was no systemic suppression of stGFP by 18 days post-infiltration (FIG. 2b, 2 days). From this result we conclude that the systemic suppression of stGFP requires T-DNA-mediated transfer of trGFP nucleic acid into plant cells.

Example 4

The Gene Silencing Signal Effects Post-transcriptional Silencing

In the tissue exhibiting the systemic suppression of stGFP, the steady state levels of stGFP RNA were reduced below the level of northern blot detection (FIG. 3 lanes 1–4) indicating that there is gene silencing. To determine whether the mechanism of stGFP silencing is transcriptional or post-transcriptional, we exploited previous demonstrations that post-transcriptionally silenced transgenes confer resistance against modified potato virus X (PVX) constructs in which there is sequence similarity to the silencer transgene[15]. A transgene exhibiting transcriptional gene silencing did not affect the corresponding viral construct[15.] The modified PVX in the present analyses (FIG. 1c) carried either a GFP or a GUS reporter gene (PVX-GFP[16] and PVX-GUS[17] respectively). The viral inocula were applied to the upper leaves of N. benthamiana at 18d post-infiltration with either water or cultures of A. tumefaciens.

Northern analysis (FIG. 3) revealed that at 5 days post-inoculation there was abundant PVX-GFP RNA in leaves of nt and stGFP N. benthamiana that had been previously infiltrated with water (FIG. 3, lanes 11–13). The PVX-GFP RNA was also abundant if the plants had been previously infiltrated with the NPT:GUS:GFP strain prepared in the presence (nt line) or absence (stGFP line) of acetosyringone (FIG. 3, lanes 9, 10, 14). However, in the stGFP-silenced leaves of plants that had been previously infiltrated with the acetosyringone-treated NPT:GUS:GFP strain of A.tumefaciens, the accumulation of PVX-GFP RNA was reduced to levels that were at or below the limit of detection (FIG. 3, lanes 5–8). When PVX-GUS was inoculated to these leaves there were as many GUS foci as on the corresponding control leaves in which there was no suppression of stGFP (FIG. 2k,l). From these differential effects on PVX-GFP and PVX-GUS we conclude that trGFP elicited sequence-specific gene silencing at the post-transcriptional level.

Example 5

The Gene Silencing Signal is not the Construct Vector or Host Comprising the Transgene Coding for the fiNA We can rule out that the systemic suppression of stGFP is associated with systemic spread of the NPT:GUS:GFP strain of A. tumefaciens because there was no detectable GUS[18] in tissues that exhibited systemic suppression of stGFP (FIG. 2h–j). Furthermore, using A selective enrichment procedure[19], we could not detect A. tumefaciens in sap extracts of tissue showing suppression of stGFP. In ten samples the selective enrichment procedure detected A.tumefaciens in $10^{-2}$-fold dilutions of infiltrated leaf extracts. However, in forty-five samples from systemic tissue (including stems and apexes) exhibiting full or partial silencing of stGFP, the infiltrated A. tumefaciens was not detected, even in undiluted samples. These sensitive assay methods therefore confirm that A. tumefaciens cells were absent from the systemic tissue in which stGFP was suppressed. We can also rule out, based on negative results of a PCR test for GUS DNA, that there is systemic movement of the NPT:GUS:GFP binary vector independently of its A. tumefaciens host.

Example 6

Effect of Reduced Levels of fiNA

In embodiments in which the fiNA is introduced into the cytoplasm by means of transcription of a nucleic acid in the nucleus, the efficient introduction of fiNA in the cytoplasm may determine the efficiency of the silencing. To verify this the systemic silencing of GFP was only partial if the GFP constructs were modified so that the 35S promoter was either deleted or replaced with the weaker nopaline synthase promoter. The resulting partial silencing was manifest as small spots on the systemic leaves of the infiltrated plants in which there was no GFP due to stGFP. The reduced gene silencing may reflect reduced levels of the GFP mRNA fiNA in the cytoplasm, owing to reduced transcription under a weaker promoter.

Example 7

The Gene Silencing Signal Does Not Require fiNA Transcription

In the second series of experiments the same stGFP plants were bombarded as young seedlings with gold particles carrying DNA fragments. When the gold particles carried sequences homologous to stGFP there was silencing of GFP as described above in the infiltrated plants after 10 d or more. These experiments revealed that the foreign nucleic acid need not be transcribed in order to elicit the systemic gene silencing.

Constructs/Nucleic Acids Used for Bombardment

All experiments described here involve GFP as a target gene in plants. Each bombardment is performed on 10 plants at the same time. Plants are small seedlings (usually 1 cm long) grown on AGAR. The indicated nucleic acids are coated onto gold particles and the bombardment of the DNA coated gold uses electrostatic acceleration such as is well known to those skilled in the art.

Each of the following constructs/nucleic acid has been tested at least 3 times (30 plants). The ability of the construct to promote silencing is expressed in term of YIELD. The yield is calculated on the 10 bombarded plants and corresponds to number of plants showing clear systemic silencing. Silencing for these purposes was taken to mean initiation within the plant of the gene silencing signal, leading to persistent silencing of the adult plant which was essentially systemic (except in meristematic tissues and in the pollen and eggs). The systemic silencing normally becomes apparent within 10 days. post bombardment and is complete after 28 days.

1. {CamV 35S promoter—GFPcDNA—Nos terminator} in PUC19

This construct gave the most elevated yield of those tested. Out of 7 independent bombardment experiments (70 plants) the average yield of silencing is 75%.

2. {GFP cDNA} in PUC19/pBluescript (GFP cDNA is 800 bp).

This construct gives silencing, but with an attenuated yield. It shows that transcription of the input homologous sequence (fiNA) is not required for setting the signal and the silencing throughout the plant.

Average yield calculated on 4 independent experiments (40 plants): 40%.

3. PCR-amplified fragment corresponding to the 5' part of the GFP cDNA, 400 bp long, no vector.

This gives silencing, with an average yield of 30% calculated on the basis on 3 experiments. This shows that even a portion of the target gene (here approximately the half) is able to generate silencing. Also, it shows that there is no need of a plasmid vector to carry the input sequence.

4. {3' part of the GFP cDNA, 300 bp long} in PUC19

This gives silencing with an average yield of 20% calculated on the basis on 2 experiments only. This shows that (i) potentially any part of the target sequence can elicit silencing and (ii) the length and/or homology between the target and the input sequence may affect the yield of silencing, but that gene silencing can be achieved with only partial sequences.

5. Control experiments

None of the following constructs led to GFP silencing:
a. {CamV 35S promoter—GUS cDNA—Nos terminator} in PUC19 tested on 60 plants
b. {Ubiquitin promoter—GUS cDNA—Nos terminator} in PUC19 tested on 60 plants
c. {400 bp of PDS cDNA} in PUC19 tested on 40 plants
d. PUC19 tested on 30 plants Example 8

Translocation of the Gene Silencing Signal is Facilitated by the Expression of a Resident Gene that is Homologous to the fiNA A three-way graft was produced in Which the bottom stock part was an stGFP *N.benthamiana* plant that had been previously infiltrated with an NPT:GUS:GFP strain of Agrobacterium as described in Example 1 and in which there was systemic silencing of GFP. The upper scion was also from an stGFP transgenic *N. benthamiana* but that had not been infiltrated and in which stGFP was not silenced. The intermediate scion was from a non-transgenic *N.benthamiana* i.e. a plant which did not comprise the GFP gene or a sequence homolog thereof. The upper part of this grafted plant remained green fluorescent over several weeks indicating that the signal did not move through the non transgenic segment that lacked a gene with homology to the fiNA. However, in Example 14 below, it was shown that after 6 weeks the signal did spread accross the graft junction in a number of cases, indicating that transcription of a homologous gene is not an absolute requirement for transmission.

In separate experiments it was confirmed that the signal of gene silencing did move efficiently though the graft union between the stock and scion of two stGFP plants.

Example 9

TIGS is Stably Maintained Whereas VIGS is Not stGFP *N. benthamiana* plants were infected with PVX-GFP to elicit 'viral induced gene silencing' ('VIGS') of GFP or were infiltrated with an NPT:GUS:GFP strain of Agrobacterium to induce TIGS. The VIGS had extended through most of the upper part of the plant by 21 days post inoculation and associated with this there was suppression of PVX-GFP below the levels detectable northern blotting. By 35 days the uppermost regions of the plants regained green fluorescence indicating that VIGS had diminished although there was no reappearance of the PVX-GFP. This suggests that VIGS requires continued presence of the initiator virus.

In the plants exhibiting TIGS of GFP the initial spread of gene silencing was at the same rate as in the plants showing VIGS. However, in these plants the silenced condition was permanent for 42 days or longer after the initial infiltration. All upper parts of the plant except the meristems, pollen and eggs exhibited silencing of GFP. The silenced condition remained even if the infiltrated leaf was detached. Thus TIGS does not require continued presence of the fiNA.

Example 10

The TIGS Can Be Maintained in Regenerated Plants

It was even possible to regenerate stGFP silenced plants by tissue culture of leaf disc explants from the upper parts of the TIGS plants. These regenerated plants showed silencing of stGFP in the same way as the original infiltrated plants.

The regeneration of gene silencing plants may be carried out by methods analogous to those used by those skilled in the art for regeneration of plants. Briefly, the regeneration was carried out as follows:

1) take a leave from a silenced plant (silenced by TIGS)
2) sterilize it for 30 minutes in 7.5% domestos
3) cut the leaf into small squares
4) put this square into "MS media plus vitamins" (Sigma) supplemented with 1.0 mg/ml of 6-BAP, 0.1 mg/ml of NAA, 3% sucrose.
5) after 2–3 weeks the squares start to produce shoots that are completely silenced (except on meristems).
6) transfer these shoots to unsupplemented "MS media plus vitamins"
7) allow the plants to grow The post transcriptional silencing was evidenced by a continued resistance to viral constructs sharing homology with the silenced gene, but no resistance to other viral constructs which did not include a GFP sequence or homolog thereof.

Example 11

The TIGS Signal Has the Characteristics of Nucleic Acid

GFP transgenic N.benthamiana were harvested at 10–20 d post infiltration with the NPT:GUS:GFP strain of agrobacterium and the leaves in which GFP expression was silenced were homogenised in phosphate buffer (50 mM pH7.0). The homogenate was then applied to the leaves of GFP N.benthamiana that had not previously been infiltrated and in which GFP expression was not silenced. The procedure for application of the sap was the same as standard procedures used to inoculate plants with virus-infected sap: the leaves were first dusted with carborundum. A drop of sap (20 uL) was applied to the leaves and the leaves were rubbed gently by hand to generate abrasions through which the sap components could enter the cells. After five minutes the leaves were drenched with water so that residual sap would not have a toxic effect.

By 20 days post treatment the GFP expression was largely unaffected. However there were several (5–20) small regions on each plant in which GFP expression (diagnosed by absence of green fluorescence under UV light) was absent. These regions varied in size between 1 and 10 mm diameter. There were no regions of GFP suppression if the extracts were taken from GFP N.benthamiana that had not previously been infiltrated with the NPT:GUS:GFP strain of agrobacterium or from non transgenic plants.

The presence of the regions suppressed GFP expression indicates that the signal of silencing had been isolated in the sap extracts. We conclude that this signal is a nucleic acid because it was heat labile (100° C. 5 min) and was not destroyed when the sap was extracted with phenol/chloroform. The signal was also not destroyed by DNAase treatment of the sap indicating that it may be RNA.

Example 12

TIGS is Not the Same as VIGS stGFP N. benthamiana were inoculated with a mutant derivatives of PVX-GFP in which the CP gene had been deleted. Because of this mutation the virus was disabled for cell to cell movement. Whereas the intact PVX-GFP elicited systemic silencing of the GFP transgene in a manner consistent with the systemic spread of the virus throughout the plants, these mutant constructs failed to do so. This failure was not because the inocula were inactive: the same inocula applied to transgenic plants expressing the PVX CP produced croning infection loci due to complementation of the CP mutation in the virus.

This result shows that VIGS did not produce a signal that moved long distances beyond the infected cells: the systemic effect of VIGS must be because the virus can move between cells. In contrast, TIGS, despite the involvement of a fiNA that is not endowed with cell to cell movement properties, does produce a long distance signal as described in the above examples.

In Examples 13 to 19 below, the stably integrated GFP transgene (trGFP) is referred to as "intGFP", while the transient FINA GFP (trGFP) is referred to as "epiGFP".

Example 13

The Gene Silencing Signal Requires Uptake of the Transgene Coding for the fiNA: The Role of T-DNA Transfer and Transcription As discussed in Example 3 above, transfer of the T-DNA from A. tumefaciens to the plant cell nucleus is a process that requires expression of the bacterial virulence (Vir) genes. To determine whether TIGS requires transfer of epiGFP into plant cells, the previously described experiments were repeated under conditions in which the A. tumefaciens Vir gene activity was either up-or down-regulated. To down-regulate the Vir genes, the A. tumefaciens culture was incubated prior to infiltration in the absence of acetosyringone, which is an inducer of Vir genes (Ream, 1989). Up-regulation of Vir genes was achieved by use of a hypervirulent strain of A. tumefaciens (cor308) carrying duplicate copies of VirG, VirE1 and VirE2 (Hamilton et al., 1996). VirG is the transcription activator of all Vir functions; VirE1 and VirE2 are involved in T-DNA transfer and stabilisation in the cytoplasm. VirE2 is also required for nuclear targeting of the T-DNA (Zupan and Zambryski, 1997).

Both approaches indicated that TIGS requires Vir gene function. Thus, with N:G:G, A. tumefaciens cultures produced in the absence of acetosyringone, the onset of TIGS was inconsistent from plant to plant and was much slower (40 d post infiltration) than with cultures prepared in the presence of acetosyringone (around 20 d post infiltration) as shown in Table I:

TABLE 1

Effect of A. tumefaciens Vir genes and epiGFP promoters on TIGS.

| Binary vector | aceto-syringone induction | hyper-virulent strain cor308 | No. of plants | No. silenced plants by 7 dpi | No. silenced plants by 20 dpi |
|---|---|---|---|---|---|
| N:G:G | + | + | 30 | 26 | 30 |
| N:G:G | + | − | 100 | 0 | 100 |
| N:G:G | − | − | 30 | 0 | 0 |
| N:G | + | − | 30 | 0 | 30 |
| N:Gnos | + | − | 30 | 0 | 30 |
| N:G Δ | + | − | 30 | 0 | 30 |

"dpi" is an abbreviation for d post infiltration. A plant was considered as silenced if there was loss of GFP fluorescence surrounding the veins of systemic leaves.

Furthermore, when cultures were produced without acetosyringone, TIGS was restricted to small discrete zones in the upper parts of the infiltrated plants and was much less extensive than in plants infiltrated with 30 acetosyringone-treated cultures. Conversely, the use of a hypervirulent *A. tumefaciens* (cor308) host of the N:G:G construct accelerated the development of TIGS by several days: TIGS initiated with this strain started at 7 d post infiltration and was complete by 10 d (Table I).

The influence of Vir gene expression indicates that TIGS requires transfer of T-DNA into plant cells. However, these experiments do not show whether epiGFP transcription is required. To address this issue, the infiltration experiments were repeated with derivatives of the pBin35S:GFP construct (FIG. 1) in which the 35S promoter of epiGFP was either replaced with the nos promoter (N:Gnos, FIG. 4). The nos promoter is much weaker than the 35S promoter of CaMV (Harpster et al., 1988). We also agroinfiltrated with a construct without a GFP promoter (N:G Δ, FIG. 4). In several experiments (Table I) there was TIGS of intGFP when the constructs were infiltrated into transgenic *N. benthamiana* plants. With both of these constructs, TIGS developed as quickly as with the original N:G:G construct (Table I), indicating that the presence of a promoter upstream epiGFP is not required for initiation of TIGS.

Example 14

Propagation of the TIGS Signal

Symplastic movement of molecules in plants can occur from cell-to-cell through plasmodesmata and/or through the phloem (Lucas et al., 1989). To investigate which of these routes is used to propagate TIGS, we monitored intGFP silencing after infiltration of plants with the N:G:G strain of *A. tumefaciens*. At 20 d post-infiltration of lower leaves, the silencing was manifest in systemic, young developing leaves and was very pronounced in the shoot tips. There was also silencing in upper leaves that were already expanded at the time of infiltration but it was fainter and less extensive than in the young developing leaves. In contrast, the leaves immediately above and below the infiltrated leaves remained fully green fluorescent. At 30 d post-infiltration the stem and roots below the infiltrated leaves also showed intGFP silencing, thus indicating that the movement of the TIGS signal was bi-directional in the plant. In terms of speed and spatial distribution, this pattern of spread is similar to the movement of viruses in the phloem, from source to sink leaves (Leisner and Turgeon, 1993).

Additional support for phloem transport of the signal comes from experiments in which intGFP plants were infiltrated with the N:G:G strain of *A. tumefaciens* in just a single leaf. These experiments differ from those described previously in which the plants were infiltrated in two or three leaves on opposite sides of the plant. At 1 month post-infiltration, intGFP silencing in the stem was restricted to the side of the original infiltrated leaf. Shoots that had emerged from the silenced portion of the stem were silenced, while those emerging from the non-silenced half were not. This pattern of signal movement was strikingly similar to the spread of a phloem-translocated dye and of a systemic virus in *N. benthamiana* (Roberts et al., 1997).

The development of silencing in leaves was also similar to the translocation of a phloem-transported dye through class I, II and III veins of *N. benthamiana* leaves (Roberts et al., 1997). In systemic leaves that had already expanded at the time of infiltration, intGFP silencing was initially (20 d post infiltration) in regions surrounding the main veins and later (27 d post-infiltration) in regions around the minor veins. At 34 d post-infiltration, intGFP silencing spread across the whole lamina of the leaf thus indicating that there was cell-to-cell movement of the silencing signal as well as translocation through the phloem. This cell-to-cell movement is likely to occur through plasmodesmata because there was no intGFP silencing in the stomatal guard cells which would have been symplastically isolated before the signal moved into the leaf (Ding et al., 1997; McLean et al., 1997). However, in leaves that developed after the signal had spread to the apical growing point, intGFP was uniformly silenced, even in the stomatal guard cells. From this observation, we conclude that guard cells are competent for gene silencing provided that the signal invades leaves early in their development, before symplastic isolation of the guard cells.

To further investigate the movement of the TIGS signal, we carried out grafting experiments similar to those described previously to characterise systemic spread of transgene-induced gene silencing (Palauqui et al., 1997; see also Example 8 above). Specifically, we wished to determine whether the signal could move through cells in which there were no genes with sequence similarity to the target of TIGS. First, to confirm that the signal is graft transmissible, we wedge-grafted non-silenced intGFP scions onto intGFP rootstocks exhibiting TIGS. TIGS spread into the scions about four weeks after the graft union in 10 out of 16 graftings tested. As with the intact N:G:G infiltrated plants, intGFP suppression in the scions was first manifest around the veins of newly emerging leaves and later became widespread on all vegetative parts of the scions.

Having thus established that the signal in this system is graft transmissible, we produced three-way grafts comprising a silenced intGFP rootstocks, an intermediate section of nt stem and a top scion of a non silenced intGFP plant. Using this procedure, we observed silencing occurring in the intGFP top scions about six weeks after the graft junctions in 5 out of 11 graftings tested. This result demonstrates that the TIGS signal could move long distances and through cells in which there is no corresponding nuclear gene, as the intermediate section had no GFP sequence.

In a separate series of experiments, the speed of signal movement was assessed by removal of the infiltrated leaf 1, 2, 3, 4 or 5 days after infiltration with the N:G:G strain of A. tumefaciens. In these experiments, there was systemic loss of intGFP fluorescence (i.e. TIGS) in 10% of the plants if the infiltrated leaf was removed 2 d post-infiltration. A progressively higher proportion of plants exhibited TIGS when the infiltrated leaf was removed 3 d or later (FIG. 5). From these data, we conclude that production and translocation of the signal occurs within 2 or 3 d post-infiltration.

In plants that exhibited TIGS after removal of the infiltrated leaf, loss of intGFP developed as quickly and persisted for as long as in the intact plants. Furthermore, in all of the N:G:G-infiltrated plants, TIGS of intGFP persisted for more than 100 d post infiltration. Even in these old plants, TIGS continued to be induced in the newly emerging leaves, despite the loss of the infiltrated leaf due to senescence. Considering these observations, we propose that propagation of the TIGS signal occurs via a relay process. The cells receiving the signal from the infiltrated leaf would become a secondary source of the signal so that maintenance of PTGS in the plant would become independent of the infiltrated leaf.

Example 15

TIGS in Meristematic Cells

Although there was extensive and persistent silencing of intGFP in the N:G:G-infiltrated *N. benthamiana* plants the floral, vegetative and root apexes always remained non silenced i.e. green fluorescent (see below). Either the signal of gene silencing cannot enter dividing cells or dividing cells lack the potential to silence intGFP. To address these alternatives, we cultured leaf explants from plants exhibiting TIGS of GFP. The explants were cultured on media promoting shoot regeneration. It was expected that intGFP silencing would be lost if dividing cells lack the potential to silence intGFP.

In shoots and leaves regenerating from these explants there was no intGFP fluorescence in most parts of the organs, whereas shoots regenerated from non-silenced plants remained fully green fluorescent. From these observations we conclude that silencing was not induced by the culture procedures but that it could persist through in vitro organogenesis. However the extreme apical regions of the silenced shoots were green fluorescent, as in the progenitor plants. When the shoots developed into plants with roots, the root tips and apical zones of vegetative and floral shoots were also green fluorescent. This apical fluorescence was not present in nontransformed plants and is therefore bona fide GFP rather than an artefact due to the presence of fluorescent compounds. These results indicate that TIGS can be maintained in, or can pass through dividing cells but that the gene silencing mechanism is not effective in meristematic tissues of the plant, presumably because the signal of TIGS cannot reach those regions. These findings reinforce the striking similarities between the movement of the TIGS signal and the movement of plant viruses, which are generally excluded from meristems (Matthews, 1991).

Example 16

Biolistic Activation of TIGS

In the experiments described above, epiGFP was delivered by infiltration of A. tumefaciens into leaves of intGFP transgenic plants. To evaluate an alternative means of epiGFP delivery, we bombarded small seedlings (5–7 mm long) with gold particles coated with the pUC 35S-GFP plasmid (FIG. 6A). This plasmid is based on pUC19 and has the complete 35S-GFP cassette from pBin35S-GFP (FIG. 6A). Three weeks after bombardment, 75% of the plants showed TIGS of intGFP. As in the agroinfiltrated plants, there was TIGS of intGFP throughout the plant except in the growing points of the shoots and roots. This result was consistent and reproducible in seven independent experiments, involving a total of 70 plants (FIG. 6A). TIGS of intGFP was never observed when intGFP plants were bombarded with uncoated gold particles or plasmid that did not carry the GFP ORF (data not shown). In order to estimate the number of cells that receive the delivered DNA, we also bombarded seedlings with a pUC 35S-GUS plasmid and stained the whole plants for GUS activity three days later. We found that, on average, less than 8 randomly distributed individual cells exhibited blue staining in whole seedlings. These results indicate that TIGS does not depend on the delivery method of epiGFP and that very localised events can initiate production and spread of the sequence-specific signal of gene silencing.

Bombardment of linear fragments of GFP cDNA without a promoter, either intact or as 5' or 3' fragments, also led to TIGS. The two fragments of GFP (..P and G..; FIG. 6A) were both less efficient initiators of TIGS than the intact cDNA (GFP, FIG. 6A) thus indicating that initiation of TIGS is affected by the length of epiGFP. To further investigate importance of epiGFP length, a series of PCR-amplified fragments were produced. These fragments were all of the same physical length (500 bp) but had 3' co-terminal fragments of GFP cDNA of varying length. The non-GFP DNA in these fragments was from pBluescript. Equal amounts of each fragment were bombarded into 50 plants in 5 independent experiments. The results, summarised in FIG. 6B, clearly show that the efficiency of TIGS initiation is determined by the length of homology between the epiGFP and the intGFP.

Example 17

TIGS Requires an Interaction of epiGFP and intGFP

In principle, TIGS could be initiated by epiGFP alone. Alternatively it could be initiated following an interaction between epiGFP and intGFP DNA or intGFP RNA. To distinguish between these possibilities, we have further characterised the targets of TIGS following bombardments with 5' or 3' linear fragments of GFP cDNA (GF. and ..P, FIG. 7A). If TIGS was initiated only by the bombarded DNA, the target would be confined to the region (i.e. sequence) of the bombarded DNA. However, a target that was determined following an interaction with intGFP could extend beyond the regions of the bombarded DNA. The assay for TIGS target sites involved inoculation of PVX-GF and PVX-P (FIG. 7A) to intGFP plants that had been bombarded 21 d previously with GFP, ..P or GF. (FIG. 7A, diagram). Virus inoculations were made to leaves exhibiting TIGS of intGFP and accumulation of the viral RNA was assessed by northern analysis of RNA samples taken from the inoculated leaves at 8d post inoculation (FIG. 7A, diagram).

Northern analyses of inoculated leaves showed that accumulation of PVX-GFP and PVX-GF (FIG. 7B, lanes 8–10 and 12–14) was lower (by at least ten fold) in leaves exhibiting TIGS of intGFP than in the leaves of non transformed plants (FIG. 7B lanes 6) or in the leaves of intGFP plants that had been previously bombarded with uncoated gold particles (FIG. 7B, lanes 6, 7 and 11). It was particularly striking that silencing induced by epi..P could target PVX-GF (FIG. 7B, lanes 13 and 14) and, conversely, silencing induced by epiGF. could target PVX-P (FIG. 7A, data not shown). As there is no sequence overlap between the GF. and ..P fragments involved in these experiments, we conclude that the target site of TIGS is determined following an interaction of epiGFP and intGFP DNA or intGFP RNA. Moreover, the influence of the bombarded DNA can extend both in the 3' (from GF to P) or in the 5' (from P to GF) direction.

Example 18

Spontaneous TIGS

Among our transgenic N. benthamiana lines, we identified one line (15a) in which intGFP systemic silencing occurs spontaneously. As with many examples of PTGS in plants, the silencing phenotype of line 15a is influenced by transgene dosage (Hobbs et al., 1993) (Mueller et al., 1995). Progeny of 15a with a hemizygous GFP transgene remained green fluorescent (data not shown) whereas those with a homozygous transgene exhibited intGFP silencing. The development of silencing in these plants followed the same pattern as in infiltrated and bombarded plants. Initially, the plants were uniformly green fluorescent but, at the four leaf stage, spots of red fluorescence developed around the veins of the upper leaves. Eventually, these regions spread along the length of the veins and throughout the plant as for TIGS induced by bombardment or infiltration of *A. tumefaciens*. We confirmed by grafting experiments the involvement of a systemic signal of silencing in line 15a. In addition, intGFP silencing was not observed in 15a meristems, as in plants exhibiting TIGS. From these observations we conclude that the bombardment or *A. tumefaciens* infiltration mimic processes that can take place spontaneously in transgenic plants.

Example 19

TIGS from Viral Constructs—Effect of Viral Proteins

A number of constucts were prepared based on the PVX-GFP amplicon constructs of PCT/GB98/00442, but included various deletions in the PVX or transgene regions. GFP was monitored under UV light.
Construction of Plasmids Referring to FIGS. 8 to 10.

The constructs were based upon pPVX209 (in which PVX-GFP is inserted into a pUC19 plasmid under a 35S promoter) which in turn was based on pPVX204 (see Baulcombe et al, 1995) but including an additional SacI site at the 5' side of the promoter.

Plasmid pPVX210A, which included a coat protein (CP) deletion, was generated from pPVX209.

Plasmids pCL100, pCL101 and pCL102, which included further deletions in the 'triple block' of cell-to-cell movement proteins (25K, 12K and 8K), were generated from pPVX210A.

Plasmid pCL105, which included further deletions in the replicase (Rep) region, was generated from PCL100.

Plasmid pCL106 included a PCR fragment from pPVX210A to restore GFP function.

Figure 10:
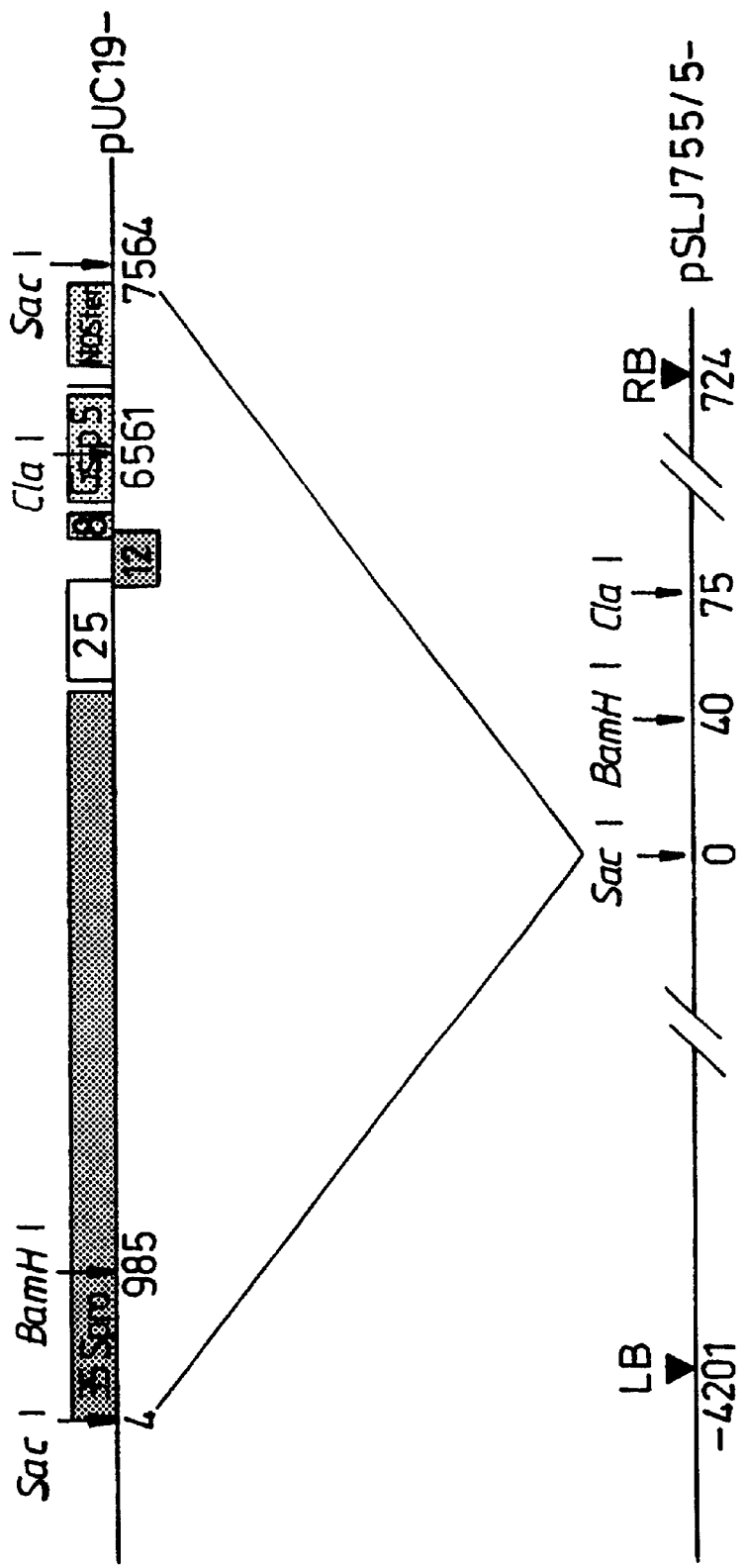

FIG. 10 shows how the pUC19 constructs were inserted into the Agrobacterium binary vector plasmid pSLJ755/5. These constructs are numbered as per Table 2:

TABLE 2

List and description of minimal constructs created (in bold type), and progenitor constructs.

| Description of construct | Construct in pUC19 | Construct in PSLJ755/5 |
|---|---|---|
| PVX-GFP-CP | pPVX209 | pPVX211 |
| PVX-GFP | pPVX210A | pPVX212A |
| PVX-ΔB-FP | pCL102 | pCL112 |
| PVX-ΔGV-FP | pCL101 | pCL111 |
| PVX-ΔTGB-FP | pCL100 | pCL110 |
| PVX-ΔRepΔTGB-FP | pCL105 | pCL115 |
| PVX-ΔTGB-GFP | pCL106 | pCL116 |
| PVX-GUS | pA500 | — |
| PVX-ΔB-GUS | pCL104 | pCL114 |
| PVX-ΔTGB-GUS | pCL103 | pCL113 |

ΔB: TGB deletion retaining 5' UTR of TGB and 5' end of 25-kDa protein gene
ΔGB: TGB deletion retaining the 5' UTR of TGB
ΔTGB: TGB deletion retaining only the first 3 nt. of the UTR of TGB The positive strand sequences for some of the constructs are given in FIG. 11.
Production and Replication of Viral RNA in Infected Cells This was confirmed in wild-type plants. Owing to the fact that movement proteins were disabled in most constructs, a standard infection assay could not be used. However, Agrobacterium strains could be infiltrated into the leaves of *N. benthamiana* to infect a high density of cells in a region of the infiltrated leaf. Northern analysis of RNA isolated from the infiltrated zone of the leaf showed that there was replication of the transcripts from constructs 212A, 110, 112 and 116 as would be predicted from their structure. The 116 construct, which included the strong CP sub-genomic promoter, produced more subgenomic RNA than other constructs. Similarly, under UV light the 212A and 116 gave bright green fluorescence—brighter than a 35S-GFP construct (pA1036—not shown) which is again consistent with replication of the constructs.
Use of Constructs to Generate TIGS Silencing of a GFP-transgenic plant was assessed as described in earlier examples in relation to non-replicating 35S-GFP constructs. The constructs described above were introduced into *Agrobacterium tumefaciens* (strain GV3101) and cultures were allowed to grow in the presence of acetosyringone. The leaves of a GFP transgenic plant were then infiltrated with the agrobacterium, as described in Example 1, and gene silencing was monitored over a four week period by UV illumination of the plants. The PVX-GFP construct in pPVX212A (see Table 2) was a less efficient silencer sequence than the PVX-Drep-DTGB-FP construct whereas the PVX-DTGB-FP (pCL110) and PVX-DTGB-GFP (PCL116) were more efficient than PVX-Drep-DTGB-FP. From these data we conclude that the ability to produce a replicating RNA, although not necessary to perform the invention, greatly enhances the efficiency of silencing but that the viral movement proteins (encoded in pPVK212A but not in PVX-DTGB-FP (pCL110) and PVX-DTGB-GFP (PCL116)) are antagonists of gene silencing. We conclude that constructs for gene silencing should be constructed so as to avoid expression of movement proteins that may antagonise the gene silencing mechanism.

Discussion of Examples 13–19

These Examples employ TIGS to further dissect PTGS into separate initiation, spread and maintenance stages. In this discussion we assess the likely molecular mechanisms of these different stages and the natural role of gene silencing in plants and other organisms. We consider the spread stage first, because the inferences about the likely nature of the signal of gene silencing influence the subsequent discussion about the initiation and maintenance stages of gene silencing.
Systemic Spread of TIGS Systemic spread of TIGS is remarkable in that it involves a sequence specific signal: TIGS initiated against GFP was specific for intGFP or viral GFP RNAs whereas TIGS against GUS was specific for GUS RNAs. This pattern of sequence specificity rules out the possibility that TIGS is a non specific wounding signal or that the specificity is related to the 35S promoter. Therefore it is likely that the signal of TIGS is specific for the transcribed regions of the target gene and that the specificity determinant includes a nucleic acid component. Thus, the signal for TIGS of GFP is likely to contain GFP RNA or DNA, whereas the signal for TIGS of GUS or other genes would contain the corresponding alternative nucleic acid species. From its pattern and speed of systemic spread, we confirm that this putative nucleic acid is able to move not only from cell to cell through plasmodesmata but also systemically through the phloem, as proposed in a recent review article (Jorgensen et al., 1998).

There are precedents in plants for endogenous nucleic acids that move between cells. For example, there are mobile nucleic acids encoded by nuclear genes including the mRNA for a transcription factor (Lucas et al., 1995) and a sucrose transporter mRNA (Kuhn et al., 1997). However in both of these examples the movement is only between cells:

there is no evidence for long distance movement, as with the signal of TIGS. The mobile nucleic acids that are most obviously comparable to the putative signal of gene silencing are viroids. Like the signal of silencing (FIG. 5), these small non-coding RNA species move systemically within a period of a few days after inoculation (Palukaitis, 1987). For both viroids and TIGS, the route of movement involves cell-to-cell through plasmodesmata and long distance spread through the phloem (Palukaitis, 1987; Ding et al., 1997).

From the leaf detachment experiment (FIG. 5), we infer that movement of the signal involves a relay. Some cells receiving the epiGFP were the primary source of initial signal production. However, once the signal moved out of the bombarded or infiltrated leaves this primary source was no longer required and there must have been cells elsewhere in the plant that were a secondary source of the signal molecule. We do not know the maximum distance between primary and secondary relay points in signal production but, from the three-way grafting experiments, we can infer that distances of several centimeters or more could be involved.

Also of interest is the deduced effect of the viral movement proteins on the spread (or possibly the initiation) of the signal (Example 19). This suggests that, while it may be desirable to have replicating constructs as a source of the fiNA, it may also be desirable to limit these to only a replicase, plus associated cis acting elements and targeting sequence, all under the control of a suitable plant promoter.

Initiation and Maintenance of Signal Production

TIGS was initiated in the bombarded or infiltrated cells that received epiGFP. It is unlikely, although it cannot formally be ruled out, that TIGS required transcription of the introduced DNA because the presence of a promoter had little or no effect on the initiation of TIGS (Table I above, plus also FIGS. 6 and 7). It is also unlikely that the signal was derived directly from the introduced DNA because TIGS induced by ..P resulted in targeting of the GF. component of GFP RNA. Similarly, bombardment of GF. produced silencing targeted against ..P (FIG. 7). Our interpretation of these data is that TIGS was initiated by an interaction between intGFP and epiGFP and that the target of TIGS was determined by intGFP. The influence of epiGFP length on TIGS is also consistent with an homology-dependent interaction between epiGFP and intGFP (FIG. 6B).

We recognise that this proposed interaction of epiGFP could involve intGFP DNA or RNA and that our data do not provide conclusive evidence for either. However, we consider that an interaction with DNA is more likely than with RNA because in N:G:G and N:G$_A$ the GFP transgene was orientated 5' to 3' towards the left border of the T-DNA (FIG. 4B). The orientation of this gene is relevant because the T-DNA of *A. tumefaciens* is transferred into plant cells as single-stranded DNA with the right border of the T-DNA at the 5' end (Zupan and Zambryski, 1997). This strand-specific transfer mechanism would not allow the single stranded epiGFP DNA to interact with intGFP RNA because both molecules have the same polarity. However, the single-stranded epiGFP T-DNA would have the potential to interact with homologous DNA in the genome, irrespective of the orientation of the insert. Consistent with a DNA-level interaction we have also shown that single stranded GFP DNA with the polarity of intGFP RNA can initiate TIGS after bombardment (data not shown).

How could a DNA-level interaction of epiGFP and intGFP result in TIGS? We propose here a mechanism similar to an earlier ectopic pairing model of PTGS in transgenic plants. According to this model, the ectopic interactions of epiGFP and intGFP would perturb transcription of the intGFP and lead ultimately to formation of anti-sense RNA (Baulcombe and English, 1996). This anti-sense RNA would target GFP RNAs for degradation and would be a component of the signal molecule. If the DNA-level interaction led to aberrant transcription of the non-coding strand of the genomic DNA, this antisense RNA could be a product of direct transcription from the genome. Alternatively the anti-sense RNA could be produced indirectly by a host-encoded RNA-dependent RNA polymerase, as suggested originally to explain transgene mediated PTGS (Lindbo et al., 1993). In this scenario the RNA-dependent RNA polymerase would produce anti-sense RNA using aberrant sense RNA as template.

The proposal that there could be ectopic interactions of homologous DNA leading to aberrant transcription is based on precedents from plants, animals and fungi. In one example, with β-globin genes in mammalian cells, an ectopic DNA interaction was demonstrated directly by the co-localisation of a transfected plasmid with the homologous sequence in the genome (Ashe et al., 1997). In plant and fungal cells, the ectopic interaction could only be inferred indirectly from the modified methylation pattern of the homologous DNAs (Hobbs et al., 1990; Barry et al., 1993). We envisage that these ectopic interactions may lead to aberrant RNA either by arrest of transcription leading to prematurely truncated RNA species, as shown in *Ascobolus immersus* (Barry et al., 1993). Alternatively the ectopic interactions could cause aberrant extension of transcription, as in the example with β-globin genes (Ashe et al., 1997).

A DNA-level interaction leading to aberrant transcription provides a convenient explanation for the persistence and uniformity of TIGS in the plant. For example, it would explain why the silenced state was stable during the lifetime of the silenced plant. The interaction of the introduced DNA or the signalling molecule at the DNA level could lead to an epigenetic change involving DNA methylation or chromatin modification that could persist even if the silenced cell was no longer receiving signal.

Consistent with this hypothesis, it has been shown that viroid RNAs can direct sequence-specific DNA methylation in transgenic plants (Wassenegger et al., 1994). Furthermore, transcription of the epimutated DNA or chromatin could provide an amplification step in TIGS. This amplification would explain the relay of TIGS and why the signal does not get diluted as it moves away from the initially infiltrated or bombarded cells.

TIGS Compared to Other Examples of Gene Silencing in Plants and Animals

Many examples of gene silencing in plants may be similar to TIGS. For example, in transgenic plants exhibiting transgene-induced PTGS, it is clear from grafting experiments (Palaugui et al., 1997) and from the spatial patterns of silencing that there is an extra-cellular signal of silencing. In addition we consider it likely that gene silencing with a delayed onset, for example with GUS transgenes, may also involve systemic spread of a signal (Elmayan and Vaucheret, 1996). In these instances, we envisage that the process may be initiated in just one or a few cells in the plant, as shown here in TIGS, and that the spread of the signal accounts for the gene silencing throughout the plant.

The involvement of a signal molecule means that genetic or epigenetic variations in single cells could influence the level of gene silencing throughout the plant. Consequently, the analysis of transgenes in whole plant DNA may not be an accurate indicator of factors that influence PTGS. For example, in a previous study based on analysis of whole plant DNA, it was concluded that single copy, hemizygous transgenes can activate PTGS (Elmayan and Vaucheret, 1996). This conclusion was difficult to reconcile with the suggestion that ectopic DNA interactions initiate PTGS (Baulcombe and English, 1996).

However, the results presented here show that the PTGS in the whole plant could have been initiated in individual cells carrying multiple copies of the transgene due to DNA endoreduplication or chromosomal rearrangements. Therefore, even in plants having only one copy of a silencer transgene in the genome, it cannot be ruled out that PTGS was initiated by ectopic interactions of homologous DNA.

Most analyses of PTGS have involved plants and fungi. However there are now reports of gene silencing phenomena in animals that appear similar to the plant and fungal systems. For example, in *Drosophila melanogaster* there is co-suppression of transgenes and endogenous genes as in petunia, tobacco and other plant systems (PalBhadra et al., 1997). However, more striking, are two recent examples of gene silencing in *Caenorhabditis elegans* (Fire et al., 1998) and in Paramecium (Ruiz et al., 1998a). The "genetic interference" described in *C. elegans* is initiated by double stranded RNA (Fire et al., 1998) rather than DNA, as described here, but otherwise shares many common features with TIGS including the ability to spread by a relay mechanism through the affected organism. In Paramecium, microinjection of plasmids containing sequences of a gene led to homology-dependent silencing of the corresponding gene in the somatic macronucleus (Ruiz et al., 1998a). As described here for TIGS, the silencing effect could be initiated with plasmids containing only the coding region of the gene and was stably maintained throughout vegetative growth of the organism. Perhaps the similarity between TIGS, the induced silencing in Paramecium and the effect of double stranded RNA in *C. elegans* reflects the existence of a ubiquitous mechanism in plants and animals that is able to specifically target aberrant RNA. This possibility fits well with the suggestion that RNA double-strandedness is a possible aberrance required for initiation of PTGS in transgenic plants (Metzlaff et al., 1997).

A Role for TIGS in Plants?

In addition to the previously made suggestion that TIGS reflects a protection mechanism in plants against viruses and transposons (Voinnet and Baulcombe, 1997—see also above), we consider it possible that TIGS also represents a natural signalling mechanism in plant development. These proposals were anticipated in an insightful review written in 1982 suggesting that viroids exploit a natural mechanism of RNA signalling (Zimmern, 1982). We consider it is possible, for example, that TIGS-like signalling may be implicated in the control of flowering in plants. It is known from classical experiments that there is a graft transmissible signal of flowering (florigen) which has many of the predicted attributes of a natural manifestation of TIGS (Poethig, 1990). Like the TIGS signal, florigen does not correspond to any of the conventionally characterised hormones or other signalling molecules in plants but it does move systemically to produce an epigenetic switch (Bernier, 1988; Colasanti et al., 1998). With florigen the epigenetic switch is associated with the transition from the vegetative to the flowering state of the plants and in TIGS, gene silencing can be considered as an epigenetic event. In some instances changes in DNA methylation have been implicated in floral commitment (Poethig, 1990). Perhaps florigen and the putative signal of TIGS are similar types of mobile RNA. This RNA might have the characteristics of viroid RNA that allow it to move systemically in plants and direct sequence specific DNA methylation (Wassenegger et al., 1994). In the case of florigen the target DNA might be sequences controlling the transition from the vegetative to the flowering state.

REFERENCES

1. Covey, S. N., Al-Kaff, N. S., Langara, A. & Turner, D. S. Plants combat infection by gene silencing. *Nature* 385, 781–782 (1997).
2. Ratcliff, F., Harrison, B. D. & Baulcombe, D. C. A similarity between viral defense and gene silencing in plants. *Science* 276, 1558–1560 (1997).
3. Assaad, F. F., Tucker, K. L. & Signer, E. R. Epigenetic repeat-induced gene silencing (rigs) in arabidopsis. *Plant Molecular Biology* 22, 1067–1085 (1993).
4. Boerjan, W., Bauw, G., Van Montagu, M. & Inzé, D. Distinct phenotypes generated by overexpression and suppression of S-Adenosyl-L-Methionine synthetase reveal developmental patterns of gene silencing in tobacco. *Plant Cell* 6, 1401–1414 (1994).
5. Matzke, M. A. & Matzke, A. J. M. How and why do plants inactivate homologous (trans)genes? *Plant Physiol.* 107, 6679–685 (1995).
6. Baulcombe, D. C. & English, J. J. Ectopic pairing of homologous DNA and post-transcriptional gene silencing in transgenic plants. *Current Opinion In Biotechnology* 7, 173–180 (1996).
7. Ingelbrecht, I., Van Houdt, H., Van Montagu, M. & Depicker, A. Posttranscriptional silencing of reporter transgenes in tobacco correlates with DNA methylation. *Proc. Natl. Acad. Sci. USA.* 91, 10502–10506 (1994).
8. Elmayan, T. & Vaucheret, H. Expression of single copies of a strongly expressed 35 S transgene can be silenced post-transcriptionally. *Plant Journal* 9, 787–797 (1996).
9. Metzlaff, M., O'Dell, M., Cluster, P. D. & Flavell, R. B. RNA-mediated RNA degradation and chalcone synthase A silencing in petunia. *Cell* 88, 845–854 (1997).
10. Mlynarova, L., Jansen, R. C., Conner, A. J., Stiekema, W. J. & Nap, J. P. The MAR-mediated reduction in position effect can be uncoupled from copy number-dependent expression in transgenic plants. *Plant Cell* 7, 599–609 (1995).
11. Chalfie, M., Tu, Y., Euskirchen, G., Ward, W. W. & Prasher, D. C. Green fluorescent protein as a marker for gene expression. *Science* 263, 802–805 (1994).
12. English, J. J., Davenport, G. F., Elmayan, T., Vaucheret, H. & Baulcombe, D. C. Requirement of sense transcription for homology-dependent virus resistance and trans-activation. *Plant Journal* (1997). (in press).
13. Vaucheret, H. Promoter-dependent trans-inactivation in transgenic tobacco plants: kinetic aspects of gene silencing and gene reactivation. *C. R. Acad. Sci. Paris.* 317, 310–323 (1994).
14. Ream, W. *Agrobacterium tumefaciens* and interkingdom genetic exchange. *Annu. Rev. Phytopathol.* 27, 583–618 (1989).
15. English, J. J., Mueller, E. & Baulcombe, D. C. Suppression of virus accumulation in transgenic plants exhibiting silencing of nuclear genes. *Plant Cell* 8, 179–188 (1996).
16. Baulcombe, D. C., Chapman, S. N. & Santa Cruz, S. Jellyfish green fluorescent protein as a reporter for virus ainfections. *Plant J.* 7, 1045–1053 (1995).
17. Chapman, S. N., Kavanagh, T. A. & Baulcombe, D. C. Potato virus X as a vector for gene expression in plants. *Plant J.* 2, 549–557 (1992).
18. Jefferson, R. A., Kavanagh, T. A. & Bevan, M. W. GUS fusions: b-glucuronidase as a sensitive and versatile gene fusion marker in higher plants. *EMBO J.* 6, 3901–3907 (1987).

19. Matzk, A, Mantell S., & Schiemann J., Localization of Persisting agrobacteria in transgenic tobacco plants. *Mol. Plant-Microbe Interact.* 9, 373–381 (1996).
20. Jorgensen, R. A. Cosuppression, flower color patterns and metastable gene expression states. *Science* 268, 686–691 (1995).
21. Kunz, C., Schöb, H., Stam, M., Kooter, J. M. & Meins, F., Jr. Developmentally regulated silencing and reactivation of tobacco chitinase transgene expression. *Plant J.* 10, 4337–450 (1996).
22. Horsch, R. B., Fry, J. E., Hoffmann, N. L., Eichholtz, D., Rogers, S. G. & Fraley, R. T. A simple and general method of transferring genes into plants. *Science* 227, 1229–1231 (1985).
23. Haseloff, J., Siemering, K. R., Prasher, D. C. & Hodge, S. Removal of a cryptic intron and subcellular localization of green fluorescent protein are required to mark transgenic Arabidopsis plants brightly. *Proc. Natl. Acad. Sci. USA* 94, 2122–2127 (1997).
24. Jefferson, R. A. Assaying chimeric genes in plants: The GUS gene fusion system. *Plant Mol. Biol.* Rep. 5, 387–405 (1987).

ADDITIONAL REFERENCES

Anandalakshmi, R., Pruss, G. J., Ge, X., Marathe, R., Smith, T. H., and Vance, V. B. (1998). A viral suppressor gene silencing in plant. Proc.Natl.Acad.Sci.USA in press.

Angell, S. M., and Baulcombe, D. C (1995). Cell to cell movement of potato virus X related by micro-injection of a viral vector tagged with the b-glucuronidase gene. Plant J. 7,135–140.

Angell, S. M., Davies, C., and Baulcombe, D. C (1996). Cell-to-cell movement of potato virus X is associated with a change in the size exclusion limit of plasmodesmata in trichome cells of *Nicotiana clevelandii.* Virology 215, 197–201.

Ashe, H. L., Monks, J., Wijgerde, M., Fraser, P., and Proudfoot, N. J. (1997). Intergenic transcription and transinduction of the human B-globin locus. Genes and Development 11, 2494–2509.

Barry, C., Faugeron, G., and Rossignol, J.-L. (1993). Methylation induced premeiotically in Ascobulus: Coextension with DNA repeat lengths and effect on transcript elongation. Proc.Natl.Acad.Sci.USA. 90, 4557–4561.

Baulcombe, D. C. (1996). Mechanisms of pathogen-derived resistance to viruses in transgenic plants. Plant Cell 8, 1833–1844.

Baulcombe, D. C., Chapman, S. N., and Santa Cruz, S. (1995). Jellyfish green fluorescent protein as a reporter for virus infections. Plant J. 7, 1045–1053.

Baulcombe, D. C., and English, J. J. (1996). Ectopic pairing of homologous DNA and post-transcriptional gene silencing in transgenic plants. Current Opinion In Biotechnology 7, 173–180.

Bernier, G. (1988). The control of floral evocation and morphogenesis. Ann. Rev. Plant Physiol. Plant Mol. Biol. 39, 175–219.

Brigneti, G., Voinne, O., Wan-Xiang, L., Liang-Hui, J., Ding, S.-W., and Baulcombe, D. C. (1998). Viral pathogenicity determinants are suppressors of transgene silencing in *Nicotiana benthamiana.* EMBO J. in press.

Chapman, S. N., Kavanagh, T. A., and Baulcombe, D. C. (1992). Potato virus X as a vector for gene expression in plants. Plant J. 2, 549–557.

Christou, P., Ford, T. L., and Kofron, M. (1991). Production of transgenic rice (*Oryza sativa* L.) plants from agronomically important indica and japonica varieties via electric discharge particle acceleration of exogenous DNA into immature zygotic embryos. Bio/Technology 9, 957–962.

Colasanti, J., Yuan, Z., and Sundaresan , V. (1998). The indeterminate Gene Encodes a Zinc Finger Protein and Regulates a Leaf-Generated Signal Required for the Transition to Flowering in Maize. Cell 93, 593–603.

Deom, C. M., Oliver, M. J., and Beachy, R. N (1987). The 30-Kilodalton Gene Produce of Tobacco Mosaic Virus Potentiates Virus Movement. Science 237, 389–394.

Depicker, A., and Van Montagu, M. (1997). Post-transcriptional gene silencing in plants. Curr. Opin. Cell Biol. 9, 372–382.

Ding, S. W., Li, W.-X., and Symons, R. H. (1995). A novel naturally occurring hybrid gene encoded by a plant RNA virus facilitates a long distance virus movement EMBO J. 14, 5762–5772.

Ding, B., Kwon, M.-O., Hammond, R., and Owens, R. (1997). Cell-to-cell movement of potato spindle tuber viroid. Plant J. 12, 931–936.

Elmayan, T., and Vaucheret, H. (1996). Expression of single copies of a strongly expressed 35S transgene can be silenced post-transcriptionally. Plant J. 9, 787–797.

English, J. J., and Baulcombe, D. C. (1997). The influence of small changes in transgene transcription on homology-dependent virus resistance and gene silencing. Plant J. 12, 1311–1318.

English, J. J., Davenport, G. F., Elmayan, T., Vaucheret, H., and Baulcombe, D. C. (1997). Requirement of sense transcription for homology-dependent virus resistance and trans-inactivation. Plant J. 12, pp.597–603.

English, J. J., Mueller, E., and Baulcombe, D. C. (1996). Suppression of virus accumulation in transgenic plants exhibiting silencing of nuclear genes. Plant Cell 8, 179–188.

Fire, A., Xu, S., Montgomery, M. K., Kostas, S. A., Driver, S. E., and Mello, C. C. (1998). Potent and specific genetic interference by double-stranded RNA in *Caenorhabditis elegans.* Nature 391, 806–811.

Hamilton, A. J., Lycett, G. W., and Grierson, D. (1990). Antisense gene that inhibits synthesis of the hormone ethylene in transgenic plants. Nature 346, 284–287.

Hamilton, C. M., Frary, A., Lewis, C., and Tanksley, S. D. (1996). Stable transfer of intact high molecular weight DNA into plant chromosomes. Proc.Natl.Acad.Sci.USA. 93, 9975–9979.

Harpster, M. H., Townsend, J. A., Jones, J. D. G., Bedbrook, J., and Dunsmuir, P. (1988). Relative strengths of the 35S cauliflower mosaic virus, 1', 2' and nopaline synthase promoters in transformed tobacco, sugarbeet and oilseed rape callus tissue. Mol.Gen.Genet. 212, 182–190.

Haseloff, J., Siemering, K. R., Prasher, D. C., and Hodge, S. (1997). Removal of a cryptic intron and subcellular localization of green fluorescent protein are required to mark transgenic Arabidopsis plants brightly. Proc.Natl.Acad.Sci.USA 94, 2122–2127.

Hobbs, S. L. A., Kpodar, P., and DeLong, C. M. O. (1990). The effect of T-DNA copy number, position and methylation on reporter gene expression in tobacco transformants. Plant Mol. Biol. 15, 851–864.

Hobbs, S. L. A., Warkentin, T. D., and DeLong, C. M. O. (1993). Transgene copy number can be positively or negatively associated with transgene expression. Plant Mol. Biol. 21, 17–26.

Horsch, R. B., Fry, J. E., Hoffmann, N. L., Eichholtz, D., Rogers, S. G., and Fraley, R. T. (1985). A simple and general method of transferring genes into plants. Science 227, 1229–1231.

Iglesias, V. A., Moscone, E. A., Papp, I., Neuhuber, F., Michalowski, S., Phelan, T., Spiker, S., Matzke, M., and Matzke, A. J. M. (1997). Molecular and cytogenetic analyses of stably and unstably expressed transgene loci in tobacco. Plant Cell 9, 1251–1264.

Jefferson, R. A. (1987). Assaying chimeric genes in plants: The GUS gene fusion system. Plant Mol.Biol.Rep. 5, 387–405.

Jones, J. D. G., Shlumukov, L., Carland, F., English, J. J., Scofield, S. R., Bishop, G., and Harrison, K. (1992). Effective vectors for transformation, expression of heterologous genes, and assaying transposon excision in transgenic plants. Transgenic Res. 1, 285–297.

Jorgensen, R. A. (1992). Silencing of plant genes by homologous transgenes. AgBiotech News and Information 4, 265–273.

Jorgensen, R. A., Atkinson, R. G., Forster, R. L. S., and Lucas, W. J. (1998). An RNA-Based Information Superhighway in Plants. Science 279, 1486–1487.

Jorgensen, R. A., Que, Q. D., English, J. J., Cluster, P., and Napoli, C. (1995). Sense-suppression of flower color genes as a sensitive reporter of epigenetic states of gene-expression in plant development. Plant Physiol. 108, 14.

Kjemtrup, S., Sampson, K. S., Peele, C. G., Nguyen, L. V., Conkling, M. A., Thompson, W. F., and Robertson, D. (1998). Gene silencing from plant DNA carried by a geminivirus. Plant J. 14, 91–100.

Kuhn, C., Franceschi, V. R., Schulz, A., Lemoine, R., and Frommer, W. B. (1997). Macromolecular Trafficking Indicated by Localization and Turnover of Sucrose Transporters in Enucleate Sieve Elements. Science 275, 1298–1300.

Kumagai, M. H., Donson, J., Della-Cioppa, G., Harvey, D., Hanley, K., and Grill, L. K. (1995). Cytoplasmic inhibition of carotenoid biosynthesis with virus-derived RNA. Proc.Natl. Acad.Sci.USA 92, 1679–1683.

Leisner, S. M., and Turgeon, R. (1993). Movement Of Virus and Photoassimilate In the Phloem—a Comparative-Analysis. Bioessays 15, 741–748.

Lindbo, J. A., Silva-Rosales, L., Proebsting, W. M., and Dougherty, W. G. (1993). Induction of a highly specific antiviral state in transgenic plants: implications for regulation of gene expression and virus resistance. Plant Cell 5, 1749–1759.

Lucas, W. J., Bouch-Pillon, S., Jackson, D. P., Nguyen, L., Baker, L., Ding, B., and Hake, S. (1995). Selective trafficking of KNOTTED1 homeodomain proteins and its mRNA through plasmodesmata. Science 270, 1980–1983.

Lucas, W. J., Wolf, S., Deom, C. M., Kishore, G. M., and Beachy, R. N. (1989). Plasmodesmata—Virus infections. unknown.

Matthews, R. E. F. (1991). Plant Virology, 3rd Edition (San Diego, Calif.: Academic Press).

McLean, B., Hempel, F., and Zambryski, P. (1997). Plant intercellular communication via plasmodesmata. The Plant Cell 9, 1043–1054.

Meins, F., Jr., and Kunz, C. (1994). Silencing of chitinase expression in transgenic plants: An autoregulatory model. In Homologous recombination and gene silencing in plants., J. Paszowski, ed. (Netherlands: Kluwer Academic Publishers), pp. 335–348.

Metzlaff, M., O'Dell, M., Cluster, P. D., and Flavell, R. B. (1997). RNA-mediated RNA degradation and chalcone synthase A silencing in petunia. Cell 88, 845–854.

Mueller, E., Gilbert, J. E., Davenport, G., Brigneti, G., and Baulcombe, D. C. (1995). Homology-dependent resistance: transgenic virus resistance in plants related to homology-dependent gene silencing. Plant J. 7, 1001–1013.

Napoli, C., Lemieux, C., and Jorgensen, R. A. (1990). Introduction of a chimeric chalcone synthase gene into Petunia results in reversible co-suppression of homologous genes in trans. Plant Cell 2, 279–289.

Palauqui, J.-C., Elmayan, T., Pollien, J.-M., and Vaucheret, H. (1997). System acquired silencing: transgene-specific post-transcriptional silencing is transmitted by grafting from silenced stocks to non-silenced scions. EMBO J. 16.

PalBhadra, M., Bhadra, U., and Birchler, J. A. (1997). Cosuppression in Drosophila: Gene silencing of Alcohol dehydrogenase by white-Adh transgenes is Polycomb dependent. Cell 90, 479–490.

Palukaitis, P. (1987). Potato Spindle Tuber Viroid: Investigation of the Long-Distance, Intra-plant Transport Route. Virology 158, 239–241.

Poethig, R. S. (1990). Phase-Change and the Regulation Of Shoot Morphogenesis In Plants. Science 250, 923–930.

Que, Q. D., Wang, H. Y., English, J. J., and Jorgensen, R. A. (1997). The frequency and degree of cosuppression by sense chalcone synthase transgenes are dependent on transgene promoter strength and are reduced by premature nonsense codons in the transgene coding sequence. Plant Cell 9, 1357–1368.

Ream, W. (1989). *Agrobacterium tumefasciens* and interkingdom genetic exchange. Annu.Rev.Phytopathol. 27, 583–618.

Roberts, A. G., Santa Cruz, S., Roberts, I. M., Prior, D. A. M., Turgeon, R., and Oparka, K. J. (1997). Phloem unloading in sink leaves of *Nicotiana benthamiana:* Comparison of a fluorescent solute with a fluorescent virus. Plant Cell 9, 1381–1396.

Ruiz, F., Vassie, L., Klotz, K., Sperling, L., and Madeddu, L. (1998a). Homology-dependent gene silencing in Paramecium. Molecular Biology Of The Cell 9, 931–943.

Ruiz, M. T., Voinnet, O., and Baulcombe, D. C. (1998b). Initiation and maintenance of virus-induced gene silencing. Plant Cell, in press.

Scholthof, H. B., Scholthof, K. B. G., and Jackson, A. O. (1995). Identification of tomato bushy stunt virus host-specific symptom determinants by expression of individual genes from a potato virus X vector. Plant Cell 7, 1157–1172.

Sijen, T., Wellink, J., Hiriart, J.-B., and van Kammen, A. (1996). RNA-mediated virus resistance: role of repeated transgenes and delineation of targeted regions. Plant Cell 8, 2277–2294.

Smith, C. J. S., Watson, C. F., Ray, J., Bird, C. R., Morris, P. C., Schuch, W., and Grierson, D. (1988). Antisense RNA inhibition of polygalaturonase gene expression in transgenic tomatoes. Nature 334, 724–726.

Stam, M., de Bruin, R., Kenter, S., van der Hoorn, R. A. L., van Blokland, R., Mol, J. N. M., and Kooter, J. M. (1997). Post-transcriptional silencing of chalcone synthase in Petunia by inverted transgene repeats. Plant J. 12, 63–82.

Vain, P., Worland, B., Kohli, A., Snape, J. W., and Christou, P. (1998). The green fluorescent protein (GFP) as a vital screenable marker in rice transformation. Theor. Appl. Genet. 96, 164–169.

Van Blokland, R., Van der Geest, N., Mol, J. N. M., and Kooter, J. M. (1994). Transgene-mediated suppression of chalcone synthase expression in Petunia hybrida results from an increase in RNA turnover. Plant J. 6, 861–877.

van der Krol, A. R., Mur, L. A., Beld, M., Mol, J. N. M., and Stuitji, A. R. (1990). Flavonoid genes in petunia: Addition of a limited number of gene copies may lead to a suppression of gene expression. Plant Cell 2, 291–299.

van Lent, J. W. M., Storms, M., van der Meer, F., Wellink, J., and Goldbach, R. W. (1991). Tubular structures involved in movement of cowpea mosaic virus are also formed in infected cowpea protoplasts. J.Gen.Virol. 72, 2615–2623.

Verchot, J., Angell, S.M., and Baulcombe, D.C. (1998). In Vivo Translation of the Entire Triple Gene Block of Potato Virus X Requires Two Separate mRNAs. J. Virol., submitted.

Voinnet, O., and Baulcombe, D. C. (1997). Systemic signalling in gene silencing. Nature 389, 553.

Wassenegger, M., Heimes, S., Riedel, L., and Sanger, H. L. (1994). RNA-directed de novo methylation of genomic sequences in plants. Cell 76, 567–576.

Wolf, S., Deom, C. M., Beachy, R. N., and Lucas, W. J (1989). Movement Protein of Tobacco Mosaic Virus Modifies Plasmodesmatal Size Exclusion Limit. Science 246, 377–379.

Yanisch-Perron, C., Vieira, J., and Messing, J. (1985). Improved M13 phage cloning vectors and host strains: nucleotide sequences of the M13mp18 and pUC19 vectors. Gene 33, 103–119.

Zimmern, D. (1982). Do viroids and RNA viruses derive from a system that exchanges genetic information between eucaryotic cells ? Trends in Biochemical Sciences, 205–207.

Zupan, J., and Zambryski, P. (1997). The Agrobacterium DNA transfer complex. Critical Reviews In Plant Sciences 16, 279–295.

What is claimed is:

1. A method for silencing a stably integrated transgene target nucleotide sequence present in a first part of a Nicotiana plant, which method comprises transiently introducing a nucleic acid construct into the cytoplasm of a cell in a second part of the plant, which cell comprises the stably integrated transgene target nucleotide sequence and which is remote from said first part of the plant, wherein said construct:
   (i) encodes a sequence which shares sequence identity with the stably integrated transgene target nucleotide sequence or the complement thereof, and
   (ii) does not encode proteins which are capable of blocking systemic movement of a gene silencing signal, such that a gene silencing signal not comprising the construct initiated in the second part of the plant and propagated to the first part of the plant such as to cause the silencing of said target nucleotide sequence in the first part of the Nicotiana plant.

2. A method as claimed in claim 1 wherein the proteins which are capable of blocking systemic movement of a gene silencing signal are those which are capable of mediating intercellular viral movement.

3. A method as claimed in claim 1 wherein the part of the plant into which the nucleic acid is introduced corresponds to a region in which photosynthetic products are concentrated and the stably integrated transgene target nucleotide sequence is present in a remote region in which such products are used.

4. A method as claimed in claim 1 wherein the stably integrated transgene target nucleotide sequence, or a nucleotide sequence sharing homology with the stable integrated transgene target nucleotide sequence, is transcribed in the cells of the tissues connecting the first and second parts of the plant through which the gene silencing signal is propagated.

5. A method as claimed in claim 1 wherein the stably integrated transgene target nucleotide sequence is silenced systemically in the plant.

6. A method as claimed in claim 1 wherein the construct is not capable of autonomous replication.

7. A method as claimed in claim 1 wherein the construct introduced into the plant cell does not encode a viral coat protein.

8. A method as claimed in claim 1 wherein the sequence sharing sequence identity with the stably integrated transgene target nucleotide sequence does not include translation-recognition signals such that said stably integrated transgene target nucleotide sequence is not translated to a protein product.

9. A method as claimed in claim 1 wherein the nucleic acid construct is DNA.

10. A method as claimed in claim 1 wherein the construct comprises a promoter operably linked to a nucleotide sequence, wherein said nucleotide sequence:
   (i) encodes a viral replicase,
   (ii) encodes a replicable sequence which shares sequence identity with the stably integrated transgene target nucleotide sequence or its complement, and which is operably linked to one or more cis acting elements recognized by said replicase, such that the replicable sequence is replicated in the cytoplasm of the cell into which it is introduced,
   (iii) does not encode proteins which are capable of mediating intercellular viral movement.

11. A method as claimed in claim 1 wherein the construct does not comprise any of the following:
   (i) promoter or terminator sequences,
   (ii) Ti-derived sequences which permit integration of the construct into the plant genome.

12. A method as claimed in claim 1 wherein the construct is introduced into the plant using *Agrobacterium tumafaciens*.

13. A method as claimed in claim 1 wherein the construct is introduced into the plant cell by microprojectile bombardment.

14. A method as claimed in claim 1 wherein the stably integrated transgene target nucleotide sequence encodes all or part of a viral genome in the plant cell.

15. A method as claimed in claim 1 wherein at least two target genes which share sequence identity are silenced.

16. A method of assessing a phenotypic charateristic associated with a stably integrated transgene target nucleotide sequence in a Nicotiana plant, the method comprising:
   (a) silencing the stably integrated transgene target nucleotide sequence in accordance with the method of claim 1,
   (b) observing the phenotype of the plan, and optionally
   (c) comparing the result of the observation with the phenotype of a control Nicotiana plant, such as to establish the phenotypic characteristic associated with the stably integrated transgene target nucleotide sequence in the Nicotiana plant.

17. A method as claimed in claim 10, wherein the viral replicase is a Potato virus X,(PVX) replicase.

18. A method as claimed in claim 10 wherein the promoter is an inducible promoter.

19. A method as claimed in claim 10 wherein the construct comprises Ti-derived sequences which permits integration of the construct into the plant genome.

20. A method as claimed in claim 10 wherein the stably integrated transgene target nucleotide sequence encodes all or part of a viral genome in the plant.

21. A method as claimed in claim 10 wherein at least two target genes which share sequence identity are silenced.

22. A method for regulating the expression of a stably integrated transgene target nucleotide sequence in a Nicotiana plant comprising the method as claimed in claim 10 which method comprises transiently introducing the nucleic acid construct into the cytoplasm of a cell in a second part of the plant, which cell comprises the stably integrated transgene target sequence and which is remote from said first part of the plant, wherein said construct:
   (i) encodes a sequence which shares sequence identity with the stably integrated transgene target nucleotide sequence or the complement thereof, and
   (ii) does not encode proteins which are capable of blocking systemic movement of a gene silencing signal such that a gene silencing signal not comprising the construct is initiated in the second part of the Nicotiana plant and propagate to the first part of the plant thereby regulating the expression of the stably integrated transgene target nucleotide sequence.

23. A method of systemically altering the phenotype of a Nicotiana plant comprising the method as claimed in claim 10 which method comprises transiently introducing the nucleic acid construct into the cytoplasm of a cell in a second part of the Nicotiana plant, which cell comprises the stably integrated transgene target nucleotide sequence and which is remote from said first part of the plant, wherein said construct:
   (i) encodes a sequence which shares sequence identity with the stably integrated transgene target nucleotide sequence or the complement thereof, and
   (ii) does not encode proteins which are capable of blocking systemic movement of a gene silencing signal such that a gene silencing signal not comprising the construct is initiated in the second part of the plant and propagated to the first part of the plant thereby systemically altering the phenotype of said Nicotiana plant.

24. A method for regulating the expression of a stably integrated transgene target nucleotide sequence present in the first part of a Nicotiana plant, which method comprises transiently introducing a nucleic acid construct into the cytoplasm of a cell in a second part of the plant, which cell comprises stably integrated transgene the target sequence and which is remote from said first part of the plant, wherein said construct:
   (i) encodes a sequence which shares sequence identity with the stably integrated transgene target nucleotide sequence or the complement thereof, and
   (ii) does not encode proteins which are capable of blocking systemic movement of a gene silencing signal, such that a gene silencing signal not comprising the construct is initiated in the second part of the plant and propagated to the first part of the Nicotiana plant thereby regulating expression of the stably integrated transgene target nucleotide sequence.

25. A method for systemically altering the phenotype of a Nicotiana plant by silencing a stably integrated transgene target nucleic acid in a first part of the plant, which method comprises transiently introducing a nucleic acid construct into the cytoplasm of a cell in a second part of the plant, which cell comprises the stably integrated transgene target nucleotide sequence and which is remote from said first part of the plant, wherein said construct:

(i) encodes a sequence which shares sequence identity with the stably integrated transgene target nucleotide sequence or the complement thereof, and (ii) does not encode proteins which are capable of blocking systemic movement of a gene silencing signal, such that a gene silencing signal not comprising the construct is initiated in the second part of the plant and propagated to the first part of the plant thereby systemically altering the phenotype of the Nicotiana plant.

* * * * *